US010668290B2

(12) United States Patent
Ghosh

(10) Patent No.: US 10,668,290 B2
(45) Date of Patent: Jun. 2, 2020

(54) DELIVERY OF PACING THERAPY BY A CARDIAC PACING DEVICE

(71) Applicant: Medtronic, Inc., Minneapolis, MN (US)

(72) Inventor: Subham Ghosh, Blaine, MN (US)

(73) Assignee: Medtronic, Inc., Minneapolis, MN (US)

(*) Notice: Subject to any disclaimer, the term of this patent is extended or adjusted under 35 U.S.C. 154(b) by 141 days.

(21) Appl. No.: 15/909,603

(22) Filed: Mar. 1, 2018

(65) Prior Publication Data

US 2019/0269926 A1  Sep. 5, 2019

(51) Int. Cl.
*A61N 1/365* (2006.01)
*A61N 1/02* (2006.01)
(Continued)

(52) U.S. Cl.
CPC ......... *A61N 1/36542* (2013.01); *A61N 1/025* (2013.01); *A61N 1/368* (2013.01);
(Continued)

(58) Field of Classification Search
CPC ........ A61N 1/368; A61N 1/365; A61N 1/372; A61N 1/3684; A61N 1/37247; A61N 1/36514; A61N 1/3682; A61N 1/36521; A61N 1/3688; A61N 1/36842; A61N 1/36843; A61N 1/3627; A61N 1/36542; A61N 1/36564; A61N 1/36571;
(Continued)

(56) References Cited

U.S. PATENT DOCUMENTS 4,233,987 A  11/1980 Feingold
4,402,323 A  9/1983 White
(Continued)

FOREIGN PATENT DOCUMENTS

CN  1043621 A  7/1990
CN  1253761 A  5/2000
(Continued)

OTHER PUBLICATIONS

International Search Report and Written Opinion dated May 3, 2012 for International Application No. PCT/US2012/036262; 9 pages.
(Continued)

*Primary Examiner* — Jon Eric C Morales

(57) ABSTRACT

A method and system for delivering cardiac pacing therapy that includes sensing electrical activity of tissue of a patient from a plurality of external electrodes during delivery of a non-ambulatory pacing therapy from a pacing device and determining an optimal electromechanical (EM) response time from an optimal electrical activation determined from electrical heterogeneity information obtained during non-ambulatory pacing therapy. During delivery of subsequent ambulatory pacing, the pacing sensing an EM signal from an EM sensor of the pacing device, determines a current EM response time in response to the sensed EM signal, and adjusting a pacing parameter setting of the ambulatory pacing therapy in response to comparing the current EM response time to the optimal EM response time.

21 Claims, 9 Drawing Sheets

(51) Int. Cl.
  *A61N 1/375*   (2006.01)
  *A61N 1/372*   (2006.01)
  *A61N 1/368*   (2006.01)
  *A61N 1/37*    (2006.01)

(52) U.S. Cl.
  CPC ......... *A61N 1/3682* (2013.01); *A61N 1/3702* (2013.01); *A61N 1/3756* (2013.01); *A61N 1/37235* (2013.01); *A61N 1/37247* (2013.01); *A61N 1/37512* (2017.08); *A61N 1/37518* (2017.08)

(58) Field of Classification Search
  CPC ............ A61N 1/36578; A61N 1/39622; A61N 1/37252; A61N 1/025; A61B 5/04085; A61B 5/0452; A61B 5/7282; A61B 5/6805
  See application file for complete search history.

(56) References Cited

U.S. PATENT DOCUMENTS

| | | |
|---|---|---|
| 4,428,378 A | 1/1984 | Anderson et al. |
| 4,497,326 A | 2/1985 | Curry |
| 4,566,456 A | 1/1986 | Koning et al. |
| 4,593,702 A | 6/1986 | Kepski |
| 4,674,511 A | 6/1987 | Cartmell |
| 4,763,660 A | 8/1988 | Kroll et al. |
| 4,777,955 A | 10/1988 | Brayten et al. |
| 4,787,389 A | 11/1988 | Tarjan |
| 4,979,507 A | 12/1990 | Heinz et al. |
| 5,052,388 A | 10/1991 | Sivula et al. |
| 5,054,496 A | 10/1991 | Wen et al. |
| 5,311,873 A | 5/1994 | Savard et al. |
| 5,331,960 A | 7/1994 | Lavine |
| 5,334,220 A | 8/1994 | Sholder |
| 5,443,492 A | 8/1995 | Stokes et al. |
| 5,485,849 A | 1/1996 | Panescu et al. |
| 5,514,163 A | 5/1996 | Markowitz et al. |
| 5,552,645 A | 9/1996 | Weng |
| 5,628,778 A | 5/1997 | Kruse et al. |
| 5,671,752 A | 9/1997 | Sinderby et al. |
| 5,683,429 A | 11/1997 | Mehra |
| 5,683,432 A | 11/1997 | Goedeke et al. |
| 5,687,737 A | 11/1997 | Branham et al. |
| 5,810,740 A | 9/1998 | Paisner |
| 5,876,336 A | 3/1999 | Swanson et al. |
| 5,891,045 A | 4/1999 | Albrecht et al. |
| 5,922,014 A | 7/1999 | Warman et al. |
| 6,055,448 A | 4/2000 | Anderson et al. |
| 6,128,535 A | 10/2000 | Maarse et al. |
| 6,141,588 A | 10/2000 | Cox et al. |
| 6,187,032 B1 | 2/2001 | Ohyu et al. |
| 6,205,357 B1 | 3/2001 | Ideker et al. |
| 6,226,542 B1 | 5/2001 | Reisfeld |
| 6,236,883 B1 | 5/2001 | Ciaccio et al. |
| 6,243,603 B1 | 6/2001 | Ideker et al. |
| 6,246,898 B1 | 6/2001 | Vesely et al. |
| 6,301,496 B1 | 10/2001 | Reisfeld |
| 6,311,089 B1 | 10/2001 | Mann et al. |
| 6,330,476 B1 | 12/2001 | Ben-Haim et al. |
| 6,358,214 B1 | 3/2002 | Tereschouk |
| 6,377,856 B1 | 4/2002 | Carson |
| 6,381,493 B1 | 4/2002 | Stadler et al. |
| 6,393,316 B1 | 5/2002 | Gillberg et al. |
| 6,418,346 B1 | 7/2002 | Nelson et al. |
| 6,442,433 B1 | 8/2002 | Linberg |
| 6,456,867 B2 | 9/2002 | Reisfeld |
| 6,473,638 B2 | 10/2002 | Ferek-Petric |
| 6,480,745 B2 | 11/2002 | Nelson et al. |
| 6,484,118 B1 | 11/2002 | Govari |
| 6,507,756 B1 | 1/2003 | Heynen et al. |
| 6,532,379 B2 | 3/2003 | Stratbucker |
| 6,584,343 B1 | 6/2003 | Ransbury et al. |
| 6,599,250 B2 | 7/2003 | Webb et al. |
| 6,625,482 B1 | 9/2003 | Panescu et al. |
| 6,640,136 B1 | 10/2003 | Helland et al. |
| 6,650,927 B1 | 11/2003 | Keidar |
| 6,766,189 B2 | 7/2004 | Yu et al. |
| 6,772,004 B2 | 8/2004 | Rudy |
| 6,804,555 B2 | 10/2004 | Warkentin |
| 6,847,836 B1 | 1/2005 | Sujdak |
| 6,856,830 B2 | 2/2005 | He |
| 6,882,882 B2 | 4/2005 | Struble et al. |
| 6,885,889 B2 | 4/2005 | Chinchoy |
| 6,915,149 B2 | 7/2005 | Ben-Haim |
| 6,937,897 B2 | 8/2005 | Min et al. |
| 6,968,237 B2 | 11/2005 | Doan et al. |
| 6,975,900 B2 | 12/2005 | Rudy et al. |
| 6,978,184 B1 | 12/2005 | Marcus et al. |
| 6,980,675 B2 | 12/2005 | Evron et al. |
| 7,016,719 B2 | 3/2006 | Rudy et al. |
| 7,027,876 B2 | 4/2006 | Casavant et al. |
| 7,031,777 B2 | 4/2006 | Hine et al. |
| 7,058,443 B2 | 6/2006 | Struble |
| 7,062,315 B2 | 6/2006 | Koyrakh et al. |
| 7,092,759 B2 | 8/2006 | Nehls et al. |
| 7,142,922 B2 | 11/2006 | Spinelli et al. |
| 7,184,835 B2 | 2/2007 | Kramer et al. |
| 7,215,998 B2 | 5/2007 | Wesselink et al. |
| 7,286,866 B2 | 10/2007 | Okerlund et al. |
| 7,308,297 B2 | 12/2007 | Reddy et al. |
| 7,308,299 B2 | 12/2007 | Burrell et al. |
| 7,313,444 B2 | 12/2007 | Pianca et al. |
| 7,321,677 B2 | 1/2008 | Evron et al. |
| 7,346,381 B2 | 3/2008 | Okerlund et al. |
| 7,398,116 B2 | 7/2008 | Edwards |
| 7,426,412 B1 | 9/2008 | Schecter |
| 7,454,248 B2 | 11/2008 | Burrell et al. |
| 7,499,743 B2 | 3/2009 | Vass et al. |
| 7,509,170 B2 | 3/2009 | Zhang et al. |
| 7,565,190 B2 | 7/2009 | Okerlund et al. |
| 7,587,074 B2 | 9/2009 | Zarkh et al. |
| 7,599,730 B2 | 10/2009 | Hunter et al. |
| 7,610,088 B2 | 10/2009 | Chinchoy |
| 7,613,500 B2 | 11/2009 | Vass et al. |
| 7,616,993 B2 | 11/2009 | Müssig et al. |
| 7,664,550 B2 | 2/2010 | Eick et al. |
| 7,684,863 B2 | 3/2010 | Parikh et al. |
| 7,742,629 B2 | 6/2010 | Zarkh et al. |
| 7,747,047 B2 | 6/2010 | Okerlund et al. |
| 7,751,882 B1 | 7/2010 | Helland et al. |
| 7,769,451 B2 | 8/2010 | Yang et al. |
| 7,778,685 B2 | 8/2010 | Evron et al. |
| 7,778,686 B2 | 8/2010 | Vass et al. |
| 7,787,951 B1 | 8/2010 | Min |
| 7,813,785 B2 | 10/2010 | Okerlund et al. |
| 7,818,040 B2 | 10/2010 | Spear et al. |
| 7,848,807 B2 | 12/2010 | Wang |
| 7,860,580 B2 | 12/2010 | Falk et al. |
| 7,894,889 B2 | 2/2011 | Zhang |
| 7,912,544 B1 | 3/2011 | Min et al. |
| 7,917,214 B1 | 3/2011 | Gill et al. |
| 7,941,213 B2 | 5/2011 | Markowitz et al. |
| 7,953,475 B2 | 5/2011 | Harlev et al. |
| 7,953,482 B2 | 5/2011 | Hess |
| 7,983,743 B2 | 7/2011 | Rudy et al. |
| 7,996,063 B2 | 8/2011 | Vass et al. |
| 7,996,070 B2 | 8/2011 | van Dam et al. |
| 8,010,194 B2 | 8/2011 | Muller |
| 8,019,402 B1 | 9/2011 | Kryzpow et al. |
| 8,019,409 B2 | 9/2011 | Rosenberg et al. |
| 8,032,229 B2 | 10/2011 | Gerber et al. |
| 8,036,743 B2 | 10/2011 | Savage et al. |
| 8,060,185 B2 | 11/2011 | Hunter et al. |
| 8,150,513 B2 | 4/2012 | Chinchoy |
| 8,160,700 B1 | 4/2012 | Ryu et al. |
| 8,175,703 B2 | 5/2012 | Dong et al. |
| 8,180,428 B2 | 5/2012 | Kaiser et al. |
| 8,195,292 B2 | 6/2012 | Rosenberg et al. |
| 8,213,693 B1 | 7/2012 | Li |
| 8,214,041 B2 | 7/2012 | Van Gelder et al. |
| 8,265,738 B1 | 9/2012 | Min et al. |
| 8,285,377 B2 | 10/2012 | Rosenberg et al. |

(56) References Cited

U.S. PATENT DOCUMENTS

| | | |
|---|---|---|
| 8,295,943 B2 | 10/2012 | Eggen et al. |
| 8,326,419 B2 | 12/2012 | Rosenberg et al. |
| 8,332,030 B2 | 12/2012 | Hess et al. |
| 8,380,308 B2 | 2/2013 | Rosenberg et al. |
| 8,401,616 B2 | 3/2013 | Verard et al. |
| 8,478,388 B2 | 7/2013 | Nguyen et al. |
| 8,509,896 B2 | 8/2013 | Doerr et al. |
| 8,527,051 B1 | 9/2013 | Hedberg et al. |
| 8,583,230 B2 | 11/2013 | Ryu et al. |
| 8,615,298 B2 | 12/2013 | Ghosh et al. |
| 8,617,082 B2 | 12/2013 | Zhang et al. |
| 8,620,433 B2 | 12/2013 | Ghosh et al. |
| 8,639,333 B2 | 1/2014 | Stadler et al. |
| 8,694,099 B2 | 4/2014 | Ghosh et al. |
| 8,738,132 B1 | 5/2014 | Ghosh et al. |
| 8,744,576 B2 | 6/2014 | Munsterman et al. |
| 8,768,465 B2 | 7/2014 | Ghosh et al. |
| 8,805,504 B2 | 8/2014 | Sweeney |
| 8,972,228 B2 | 3/2015 | Ghosh et al. |
| 9,037,238 B2 | 5/2015 | Stadler et al. |
| 9,155,897 B2 | 10/2015 | Ghosh et al. |
| 9,199,087 B2 | 12/2015 | Stadler et al. |
| 9,265,951 B2 | 2/2016 | Sweeney |
| 9,265,954 B2 | 2/2016 | Ghosh |
| 9,265,955 B2 | 2/2016 | Ghosh |
| 9,278,219 B2 | 3/2016 | Ghosh |
| 9,278,220 B2 | 3/2016 | Ghosh |
| 9,282,907 B2 | 3/2016 | Ghosh |
| 9,320,446 B2 | 4/2016 | Gillberg et al. |
| 9,474,457 B2 | 10/2016 | Ghosh et al. |
| 9,486,151 B2 | 11/2016 | Ghosh et al. |
| 9,510,763 B2 | 12/2016 | Gosh et al. |
| 9,586,050 B2 | 3/2017 | Ghosh et al. |
| 9,586,052 B2 | 3/2017 | Gillberg et al. |
| 9,591,982 B2 | 3/2017 | Ghosh et al. |
| 9,764,143 B2 | 9/2017 | Ghosh et al. |
| 9,776,009 B2 | 10/2017 | Ghosh et al. |
| 2002/0072682 A1 | 6/2002 | Hopman et al. |
| 2002/0087089 A1 | 7/2002 | Ben-Haim |
| 2002/0143264 A1 | 10/2002 | Ding et al. |
| 2002/0161307 A1 | 10/2002 | Yu et al. |
| 2002/0169484 A1 | 11/2002 | Mathis et al. |
| 2003/0018277 A1 | 1/2003 | He |
| 2003/0050670 A1 | 3/2003 | Spinelli et al. |
| 2003/0105495 A1 | 6/2003 | Yu et al. |
| 2003/0236466 A1 | 12/2003 | Tarjan et al. |
| 2004/0015081 A1 | 1/2004 | Kramer et al. |
| 2004/0059237 A1 | 3/2004 | Narayan et al. |
| 2004/0097806 A1 | 5/2004 | Hunter et al. |
| 2004/0102812 A1 | 5/2004 | Yonce et al. |
| 2004/0122479 A1 | 6/2004 | Spinelli et al. |
| 2004/0162496 A1 | 8/2004 | Yu et al. |
| 2004/0172078 A1 | 9/2004 | Chinchoy |
| 2004/0172079 A1 | 9/2004 | Chinchoy |
| 2004/0193223 A1 | 9/2004 | Kramer et al. |
| 2004/0215245 A1 | 10/2004 | Stahmann et al. |
| 2004/0215252 A1 | 10/2004 | Verbeek et al. |
| 2004/0220635 A1 | 11/2004 | Burnes |
| 2004/0267321 A1 | 12/2004 | Boileau et al. |
| 2005/0008210 A1 | 1/2005 | Evron et al. |
| 2005/0027320 A1 | 2/2005 | Nehls et al. |
| 2005/0090870 A1 | 4/2005 | Hine et al. |
| 2005/0096522 A1 | 5/2005 | Reddy et al. |
| 2005/0107839 A1 | 5/2005 | Sanders |
| 2005/0149138 A1 | 7/2005 | Min et al. |
| 2006/0074285 A1 | 4/2006 | Zarkh et al. |
| 2006/0224198 A1 | 10/2006 | Dong et al. |
| 2006/0235478 A1 | 10/2006 | Van Gelder et al. |
| 2006/0253162 A1 | 11/2006 | Zhang et al. |
| 2007/0142871 A1 | 6/2007 | Libbus et al. |
| 2007/0232943 A1 | 10/2007 | Harel et al. |
| 2007/0250129 A1 | 10/2007 | Van Oort |
| 2007/0265508 A1 | 11/2007 | Sheikhzadeh-Nadjar et al. |
| 2008/0021336 A1 | 1/2008 | Dobak et al. |
| 2008/0058656 A1 | 3/2008 | Costello et al. |
| 2008/0119903 A1 | 5/2008 | Arcot-Krishnamurthy et al. |
| 2008/0140143 A1 | 6/2008 | Ettori et al. |
| 2008/0146954 A1 | 6/2008 | Bojovic et al. |
| 2008/0242976 A1 | 10/2008 | Robertson et al. |
| 2008/0269818 A1 | 10/2008 | Sullivan et al. |
| 2008/0269823 A1 | 10/2008 | Burnes et al. |
| 2008/0281195 A1 | 11/2008 | Heimdal |
| 2008/0306567 A1 | 12/2008 | Park et al. |
| 2008/0306568 A1 | 12/2008 | Ding et al. |
| 2009/0005832 A1 | 1/2009 | Zhu et al. |
| 2009/0036947 A1 | 2/2009 | Westlund et al. |
| 2009/0043352 A1 | 2/2009 | Brooke et al. |
| 2009/0048528 A1 | 2/2009 | Hopenfeld et al. |
| 2009/0053102 A2 | 2/2009 | Rudy et al. |
| 2009/0054941 A1 | 2/2009 | Eggen et al. |
| 2009/0054946 A1 | 2/2009 | Sommer et al. |
| 2009/0084382 A1 | 4/2009 | Jalde et al. |
| 2009/0093857 A1 | 4/2009 | Markowitz et al. |
| 2009/0099468 A1 | 4/2009 | Thiagalingam et al. |
| 2009/0099469 A1 | 4/2009 | Flores |
| 2009/0099619 A1 | 4/2009 | Lessmeier et al. |
| 2009/0112109 A1 | 4/2009 | Kuklik et al. |
| 2009/0143838 A1 | 6/2009 | Libbus et al. |
| 2009/0157134 A1 | 6/2009 | Ziglio et al. |
| 2009/0157136 A1 | 6/2009 | Yang et al. |
| 2009/0198298 A1 | 8/2009 | Kaiser et al. |
| 2009/0216112 A1 | 8/2009 | Assis et al. |
| 2009/0232448 A1 | 9/2009 | Barmash et al. |
| 2009/0234414 A1 | 9/2009 | Sambelashvili et al. |
| 2009/0254140 A1 | 10/2009 | Rosenberg et al. |
| 2009/0270729 A1 | 10/2009 | Corbucci et al. |
| 2009/0270937 A1 | 10/2009 | Yonce et al. |
| 2009/0299201 A1 | 12/2009 | Gunderson |
| 2009/0299423 A1 | 12/2009 | Min |
| 2009/0306732 A1 | 12/2009 | Rosenberg et al. |
| 2009/0318995 A1 | 12/2009 | Keel et al. |
| 2010/0022873 A1 | 1/2010 | Hunter et al. |
| 2010/0049063 A1 | 2/2010 | Dobak, III |
| 2010/0069987 A1 | 3/2010 | Min et al. |
| 2010/0087888 A1 | 4/2010 | Maskara |
| 2010/0094149 A1 | 4/2010 | Kohut et al. |
| 2010/0113954 A1 | 5/2010 | Zhou |
| 2010/0114229 A1 | 5/2010 | Chinchoy |
| 2010/0121403 A1 | 5/2010 | Schecter et al. |
| 2010/0145405 A1 | 6/2010 | Min et al. |
| 2010/0174137 A1 | 7/2010 | Shim |
| 2010/0198292 A1 | 8/2010 | Honeck et al. |
| 2010/0228138 A1 | 9/2010 | Chen |
| 2010/0234916 A1 | 9/2010 | Turcott et al. |
| 2010/0249622 A1 | 9/2010 | Olson |
| 2010/0254583 A1 | 10/2010 | Chan et al. |
| 2010/0268059 A1 | 10/2010 | Ryu et al. |
| 2011/0004111 A1 | 1/2011 | Gill et al. |
| 2011/0004264 A1 | 1/2011 | Siejko et al. |
| 2011/0022112 A1 | 1/2011 | Min |
| 2011/0054286 A1 | 3/2011 | Crosby |
| 2011/0054559 A1 | 3/2011 | Rosenberg et al. |
| 2011/0054560 A1 | 3/2011 | Rosenberg et al. |
| 2011/0075896 A1 | 3/2011 | Matsumoto |
| 2011/0092809 A1 | 4/2011 | Nguyen et al. |
| 2011/0112398 A1 | 5/2011 | Zarkh et al. |
| 2011/0118803 A1 | 5/2011 | Hou et al. |
| 2011/0137369 A1 | 6/2011 | Ryu et al. |
| 2011/0144510 A1 | 6/2011 | Ryu et al. |
| 2011/0172728 A1 | 7/2011 | Wang |
| 2011/0190615 A1 | 8/2011 | Phillips et al. |
| 2011/0201915 A1 | 8/2011 | Gogin et al. |
| 2011/0213260 A1 | 9/2011 | Keel et al. |
| 2011/0319954 A1 | 12/2011 | Niazi et al. |
| 2012/0004567 A1 | 1/2012 | Eberle et al. |
| 2012/0101543 A1 | 4/2012 | Demmer et al. |
| 2012/0101546 A1 | 4/2012 | Stadler et al. |
| 2012/0203090 A1 | 8/2012 | Min |
| 2012/0253419 A1 | 10/2012 | Rosenberg et al. |
| 2012/0283587 A1 | 11/2012 | Ghosh et al. |
| 2012/0284003 A1 | 11/2012 | Ghosh et al. |
| 2012/0296387 A1 | 11/2012 | Zhang et al. |
| 2012/0296388 A1 | 11/2012 | Zhang et al. |
| 2012/0302904 A1 | 11/2012 | Lian et al. |

(56) References Cited

U.S. PATENT DOCUMENTS

| | | |
|---|---|---|
| 2012/0303084 A1 | 11/2012 | Kleckner et al. |
| 2012/0310297 A1 | 12/2012 | Sweeney |
| 2012/0330179 A1 | 12/2012 | Yuk et al. |
| 2013/0006332 A1 | 1/2013 | Sommer et al. |
| 2013/0018250 A1 | 1/2013 | Caprio et al. |
| 2013/0018251 A1 | 1/2013 | Caprio et al. |
| 2013/0030491 A1 | 1/2013 | Stadler et al. |
| 2013/0060298 A1 | 3/2013 | Splett et al. |
| 2013/0072790 A1 | 3/2013 | Ludwig et al. |
| 2013/0096446 A1 | 4/2013 | Michael et al. |
| 2013/0116739 A1 | 5/2013 | Brada et al. |
| 2013/0131529 A1 | 5/2013 | Jia et al. |
| 2013/0131749 A1 | 5/2013 | Sheldon et al. |
| 2013/0131751 A1 | 5/2013 | Stadler et al. |
| 2013/0136035 A1 | 5/2013 | Bange et al. |
| 2013/0150913 A1 | 6/2013 | Bornzin et al. |
| 2013/0165983 A1 | 6/2013 | Ghosh et al. |
| 2013/0165988 A1 | 6/2013 | Ghosh |
| 2013/0261471 A1 | 10/2013 | Saha et al. |
| 2013/0261688 A1 | 10/2013 | Dong et al. |
| 2013/0289640 A1 | 10/2013 | Zhang et al. |
| 2013/0296726 A1 | 11/2013 | Niebauer et al. |
| 2013/0304407 A1 | 11/2013 | George et al. |
| 2013/0324828 A1 | 12/2013 | Nishiwaki et al. |
| 2014/0005563 A1 | 1/2014 | Ramanathan et al. |
| 2014/0018872 A1 | 1/2014 | Siejko et al. |
| 2014/0135866 A1 | 5/2014 | Ramanathan et al. |
| 2014/0135867 A1 | 5/2014 | Demmer et al. |
| 2014/0163633 A1 | 6/2014 | Ghosh et al. |
| 2014/0222099 A1 | 8/2014 | Sweeney |
| 2014/0236252 A1 | 8/2014 | Ghosh et al. |
| 2014/0276125 A1 | 9/2014 | Hou et al. |
| 2014/0277233 A1 | 9/2014 | Ghosh |
| 2014/0323882 A1 | 10/2014 | Ghosh et al. |
| 2014/0323892 A1 | 10/2014 | Ghosh et al. |
| 2014/0323893 A1 | 10/2014 | Ghosh et al. |
| 2014/0371807 A1 | 12/2014 | Ghosh et al. |
| 2014/0371808 A1 | 12/2014 | Ghosh et al. |
| 2014/0371832 A1 | 12/2014 | Ghosh et al. |
| 2014/0371833 A1 | 12/2014 | Ghosh et al. |
| 2015/0032016 A1 | 1/2015 | Ghosh |
| 2015/0032171 A1 | 1/2015 | Ghosh |
| 2015/0032172 A1 | 1/2015 | Ghosh |
| 2015/0032173 A1 | 1/2015 | Ghosh |
| 2015/0045849 A1 | 2/2015 | Ghosh et al. |
| 2015/0142069 A1 | 5/2015 | Sambelashvili |
| 2015/0157225 A1 | 6/2015 | Gillberg et al. |
| 2015/0157231 A1 | 6/2015 | Gillberg et al. |
| 2015/0157232 A1 | 6/2015 | Gillberg et al. |
| 2015/0157865 A1 | 6/2015 | Gillberg et al. |
| 2015/0216434 A1 | 8/2015 | Ghosh et al. |
| 2015/0265840 A1 | 9/2015 | Ghosh et al. |
| 2016/0030747 A1 | 2/2016 | Thakur et al. |
| 2016/0030751 A1 | 2/2016 | Ghosh et al. |
| 2016/0045737 A1* | 2/2016 | Ghosh .................. A61N 1/3684 607/17 |
| 2016/0045738 A1 | 2/2016 | Ghosh et al. |
| 2016/0045744 A1 | 2/2016 | Gillberg et al. |
| 2016/0184590 A1 | 6/2016 | Ghosh |
| 2017/0303840 A1 | 10/2017 | Stadler et al. |
| 2018/0140847 A1* | 5/2018 | Taff .................. A61N 1/36521 |

FOREIGN PATENT DOCUMENTS

| | | |
|---|---|---|
| CN | 1878595 A | 12/2006 |
| CN | 101073502 A | 11/2007 |
| EP | 1 072 284 A2 | 1/2001 |
| EP | 1 504 713 A1 | 2/2005 |
| EP | 2 016 976 A1 | 1/2009 |
| EP | 2 391 270 A1 | 7/2011 |
| EP | 1 925 337 B1 | 3/2012 |
| EP | 2 436 309 A2 | 4/2012 |
| EP | 2 435 132 B1 | 8/2013 |
| WO | WO 1998/026712 A1 | 6/1998 |
| WO | WO 1999/006112 A1 | 2/1999 |
| WO | WO 2000/045700 A1 | 8/2000 |
| WO | WO 2001/067950 A1 | 9/2001 |
| WO | WO 2003/070323 A1 | 8/2003 |
| WO | WO 2005/056108 A2 | 6/2005 |
| WO | WO 2006/069215 A2 | 6/2006 |
| WO | WO 2006/105474 A2 | 10/2006 |
| WO | WO 2006/115777 A1 | 11/2006 |
| WO | WO 2006/117773 A1 | 11/2006 |
| WO | WO 2007/013994 A2 | 2/2007 |
| WO | WO 2007/027940 A2 | 3/2007 |
| WO | WO 2007/013994 A3 | 4/2007 |
| WO | WO 2007/027940 A3 | 6/2007 |
| WO | WO 2007/139456 A1 | 12/2007 |
| WO | WO 2008/151077 A2 | 12/2008 |
| WO | WO 2006/069215 A3 | 6/2009 |
| WO | WO 2009/079344 A1 | 6/2009 |
| WO | WO 2009/139911 A2 | 11/2009 |
| WO | WO 2009/148429 A1 | 12/2009 |
| WO | WO 2010/019494 A1 | 2/2010 |
| WO | WO 2010/071520 A1 | 6/2010 |
| WO | WO 2010/088040 A1 | 8/2010 |
| WO | WO 2010/088485 A1 | 8/2010 |
| WO | WO 2011/070166 A1 | 6/2011 |
| WO | WO 2011/090622 A1 | 7/2011 |
| WO | WO 2011/099992 A1 | 8/2011 |
| WO | WO 2012/0374711 A2 | 3/2012 |
| WO | WO 2012/037471 A3 | 6/2012 |
| WO | WO 2012/106297 A2 | 8/2012 |
| WO | WO 2012/106297 A3 | 8/2012 |
| WO | WO 2012/109618 A2 | 8/2012 |
| WO | WO 2012/110940 A1 | 8/2012 |
| WO | WO 2012/109618 A3 | 11/2012 |
| WO | WO 2012/151364 A1 | 11/2012 |
| WO | WO 2012/151389 A1 | 11/2012 |
| WO | WO 2013/006724 A2 | 1/2013 |
| WO | WO 2013/010165 A1 | 1/2013 |
| WO | WO 2013/010184 A1 | 1/2013 |
| WO | WO 2013/006724 A3 | 4/2013 |
| WO | WO 2014/179454 A1 | 11/2014 |
| WO | WO 2014/179459 A2 | 11/2014 |
| WO | WO 2014/179459 A3 | 1/2015 |
| WO | WO 2015/013271 A1 | 1/2015 |
| WO | WO 2015/013493 A1 | 1/2015 |
| WO | WO 2015/013574 A1 | 1/2015 |

OTHER PUBLICATIONS

International Search Report and Written Opinion dated May 3, 2012 for International Application No. PCT/US2012/036302; 9 pages.
International Search Report and Written Opinion dated Aug. 6, 2014 for International Application No. PCT/US2014/036153; 14 pages.
International Search Report and Written Opinion dated Nov. 7, 2014 for International Application No. PCT/US2014/036163; 12 pages.
International Search Report and Written Opinion dated Oct. 28, 2014 for International Application No. PCT/US2014/041928; 15 pages.
International Search Report and Written Opinion dated Oct. 24, 2014 for International Application No. PCT/US2014/041929; 14 pages.
International Search Report and Written Opinion dated Nov. 4, 2014 for International Application No. PCT/US2014/0247583; 7 pages.
International Search Report and Written Opinion dated Nov. 12, 2014 for International Application No. PCT/US2014/047971; 7 pages.
International Search Report and Written Opinion dated Nov. 12, 2014 for International Application No. PCT/US2014/048120; 7 pages.
International Search Report and Written Opinion dated Mar. 9, 2015 for International Application No. PCT/US2014/069214; 11 pages.
International Search Report and Written Opinion dated Mar. 17, 2015, for International Application No. PCT/US2014/069192; 11 pages.
International Search Report and Written Opinion dated Mar. 16, 2015 for International Application No. PCT/US2014/069182; 11 pages.

(56) References Cited

OTHER PUBLICATIONS

International Search Report and Written Opinion dated Apr. 8, 2015 for International Application No. PCT/US2014/069070; 11 pages.
International Search Report and Written Opinion dated Jun. 11, 2015 for International Application No. PCT/US2015/021442; 13 pages.
Biffi et al., "Occurrence of Phrenic Nerve Stimulation in Cardiac Resynchronization Therapy Patients: the Role of Left Ventricular Lead Type and Placement Site," Europace, 2013; 15:77-82.
Botker MD, PhD., et al., "Electromechanical Mapping for Detection of Myocardial Viability in Patients with ischemia Cardiomyopathy," Circulation, Mar. 2001; vol. 103, No. 12, pp.
"CardioGuide System Enables Real-Time Navigation of Left Ventricular Leads During Medtronic CRT Implants," Press Release, Apr. 9, 2013, Medtronic, Inc., 2 pgs.
Cuculich, P.S., et al., "The Electrophysiological Cardiac Ventricular Substrate in Patients After Myocardial Infection" J. Am. Coll. Cardiol. 2011; 58:1893-1902.
Czerwinska et al., "Method of Segmentation of Thorax Organs Images Applied to Modeling the Cardiac Electrical Field," Engineering in Medicine and Biology Society, Proceedings of the $22^{nd}$ Annual International Conference of the IEEE, vol. 1, 23, Jul. 23, 2000.; pp. 402-405.
Dawoud, F. et al., "Inverse Electrocardiographic Imaging to Assess Electrical Dyssynchrony in Cardiac Resynchronization Therapy Patients," Computing in Cardiology, 2012; 39:993-996.
Freund et al., "A Decision-Theoretic Generalization of Online Learning and an Application to Boosting," Journal of Computer and System Sciences, 1997; 55(1):119-139.
Friedman, "Greedy Function Approximation: A Gradient Boosting Machine," Annals of Statistics, 2001; 29(5):1189-1232.
Friedman, "Stochastic Gradient Boosting," Computational Statistics and Data Analysis, 2002; 38(4):367-378.
Friedman et al., "Additive Logistic Regression: a Statistical View of Boosting," Annals of Statistics, 2000; 28(2):337-374.
Fung et al., Chapter 20, Optimization of Cardiac Resynchronization Therapy, Cardiac Resynchronization Therapy, Second Edition, Copyright 2008, Blackwell Publishing Ltd., pp. 356-373.
Ghosh et al. "Accuracy of Quadratic Versus Linear Interpolation in Noninvasive Electrocardiographic Imaging (ECGI)," Annuals of Biomedical Engineering, vol. 33, No. 9. Sep. 2005; pp. 1187-1201.
Ghosh et al., "Cardiac Memory in Patients with Wolff-Parkinson—White Syndrome: Noninvasive Imaging of Activation and Repolarization Before and After Catheter Ablation" Circulation, 2008; 118:907-915. Published online Aug. 12, 2008.
Ghosh et al. "Application of L1-Norm Regularization to Epicardial Potential Solution of the Inverse Electrocardiography Problem," Annuals of Biomedical Engineering, vol. 37, No. 5, May 2009; pp. 902-912.
Ghosh et al., "Electrophysiological Substrate and Intraventricular LV Dyssynchrony in Non-ischemic Heart Failure Patients Undergoing Cardiac Resynchronization Therapy," Heart rhythm : the official journal of the Heart Rhythm Society, 2011; 8(5):692-699.
Gold et al., "Comparison of Stimulation Sites within Left Ventricular Veins on the Acute Hemodynamic Effects of Cardiac Resynchronization Therapy" Heart Rhythm, Apr. 2005; 2(4): 376-381.
Gulrajani, "The Forward and Inverse Problems of Electrocardiography," IEEE Engineering in Medicine and Biology, IEEE Service Center, vol. 17, No. 5, Sep. 1, 1988; pp. 84-101, 122.
Hansen, "Regularization Tools: A Matlab Package for Analysis and Solution of Discrete III-Posed Problems," Version 4.1 for Matlab 7.3; Mar. 2008; 128 pages. Retrieved from the Internet: Jun. 19, 2014 http://www.mathworks.com/matlabcentral/fileexchange/52-regtools.
Hayes et al., "Cardiac Resynchronization Therapy and the Relationship of Percent Biventricular Pacing to Symptoms and Survival," Heart Rhythm, Sep. 2011; 8(9):1469-1475.
"Heart Failure Management" datasheet [online]. Medtronic, Minneapolis, Minnesota, [Last updated on Jun. 3, 2013].Retrieved from the Internet: www.medtronic.com; 9 pages.
Hopenfeld et al., "The Effect of Conductivity on ST—Segment Epicardial Potentials Arising from Subendocardial Ischemia," Annals of Biomedical Eng., Jun. 2005; vol. 33, No. 6, pp. 751-763.
Jia et al., "Electrocardiographic Imaging of Cardiac Resynchronization Therapy in Heart Failure: Observation of Variable Electrophysiologic Responses," Heart Rhythm, vol. 3, No. 3; Mar. 1, 2006, pp. 296-310.
Kornreich, "Body Surface Potential Mapping of ST Segment Changes in Acute Myocardial Infarction," Circulation, 1993; 87: 773-782.
Lumason™, Brochure, Bracco Diagnostocs. Oct. 2014.
Medtronic Vitatron CARELINK ENCORE® Programmer Model 29901 Reference Manual, 2013, Medtronic, Inc., Minneapolis, MN.
Miri et al., "Applicability of body surface potential map in computerized optimization of biventricular pacing," Annals of Biomedical Engineering, vol. 38, No. 3, Mar. 2010, pp. 865-875.
Miri et al., "Comparison of the electrophysiologically based optimization methods with different pacing parameters in patient undergoing resynchronization treatment," 30th Annual International IEEE EMBS Conference, Aug. 2008, pp. 1741-1744.
Miri et al., "Computerized Optimization of Biventricular Pacing Using Body Surface Potential Map," 31st Annual International Conference of the IEEE EMBS, Sep. 2009, pp. 2815-2818.
Miri et al., "Efficiency of Timing Delays and Electrode Positions in Optimization of Biventricular Pacing: A Simulation Study," IEEE Transactions on Biomedical Engineering, Nov. 2009, pp. 2573-2582.
Modre et al., "Noninvasive Myocardial Activation Time Imaging: A Novel Inverse Algorithm Applied to Clinical ECG Mapping Data" IEEE Transactions on Biomedical Engineering, vol. 49; No. 10, Oct. 2002; pp. 1153-1161.
Nash et al., "An Experimental-Computational Framework for Validating in-vivo ECG Inverse Algorithms," International Journal of Bioelectromagnetism, vol. 2, No. 2, Dec. 31, 2000, 9 pp.
Potse et al., "Mathematical Modeling and Simulation of Ventricular Activation Sequences: Implications for Cardiac Resynchronization Therapy," J. of Cardiovasc. Trans. Res., 2012; 5:146-158.
Prinzen et al., "Cardiac Resynchronization Therapy State-of-the-Art of Current Applications, Guidelines, Ongoing Trials, and Areas of Controversy" Circulation, 2013; 128: 2407-2418.
Ridgeway, "The State of Boosting," Computing Science and Statistics, 1999; 31:172-181.
Ryu et al., "Simultaneous Electrical and Mechanical Mapping Using 3D Cardiac Mapping System: Novel Approach for Optimal Cardiac Resynchronization Therapy," Journal of Cardiovascular Electrophysiology, Feb. 2010; 21(2):219-22.
Silva et al., "Cardiac Resynchronization Therapy in Pediatric Congenital Heart Disease: Insights from Noninvasive Electrocardiographic Imaging" Heart Rhythm, vol. 6, No. 8. Aug. 1, 2009; pp. 1178-1185.
Singh et al., "Left Ventricular Lead Position and Clinical Outcome in the Multicenter Automatic Defibrillator Implantation Trial-Cardiac Resynchronization Therapy (MADIT-CRT) Trial," Circulation, 2011; 123:1159-1166.
Sperzel et al., "Intraoperative Characterization of Interventricular Mechanical Dyssynchrony Using Electroanatomic Mapping System—A Feasibility Study," Journal of Interventional Cardiac Electrophysiology, Nov. 2012; 35(2):189-96.
Steinhaus BM., "Estimating cardiac transmembrane activation and recovery times from unipolar and bipolar extracellular electrograms: a simulation study," Circulation Research, 1989, 64:449-462.
Strik et al., "Electrical and Mechanical Ventricular Activation During Left Bundle Branch Block and Resynchronization," J. of Cardiovasc. Trans. Res., 2012; 5:117-126.
Svendsen et al., "Computational Models of Cardiac Electrical Activation," Chapter 5, Computational Nov. 2010, pp. 73-88.
Sweeney et al., "Analysis of Ventricular Activation Using Surface Electrocardiography to Predict Left Ventricular Reverse Volumetric Remodeling During Cardiac Resynchronization Therapy," Circulation, Feb. 9, 2010;121(5):626-34. Available online Jan. 25, 2010.
Sweeney et al., QRS Fusion Complex Analysis Using Wave Interference to Predict Reverse Remodeling During Cardiac Resynchronization Therapy, heart Rhythm, 2014, 11:806-813.

(56) References Cited

OTHER PUBLICATIONS

Turner et al, "Electrical and Mechanical Components of Dyssynchrony in Heart Failure Patients with Normal QRS Duration and Left Bundle-Branch Block," *Circulation* 2004; 109:2544-2549.

Van Deursen et al., "Vectorcardiography as a Tool for Easy Optimization of Cardiac Resynchronization Therapy in Canine LBBB Hearts," *Circulation Arrhythmia and Electrophysiology*, Jun. 1, 2012; 5(3):544-52. Available online Apr. 24, 2012.

Vardas et al., The Task Force for Cardiac Pacing and Cardiac Resynchronization Therapy of the European Society of Cardiology. Developed in Collaboration with the European Heart Rhythm Association, *European Heart Journal*, 2007; 28:2256-2295.

Varma et al., "Placebo CRT," *Journal of Cardiovascular Electrophysiology*, vol. 19, Aug. 2008; p. 878.

Wang et al., "Application of the Method of Fundamental Solutions to Potential-based Inverse Electrocardiography," Annals of Biomedical Engineering, Aug. 2006, pp. 1272-1288.

Wellens, MD et al., "The Electrocardiogram 102 Years After Einthoven," Circulation, Feb. 2004; vol. 109, No. 5, pp. 562-564.

Williams et al., "Short-Term Hemodynamic Effects of Cardiac Resynchronization Therapy in Patients With Heart Failure, a Narrow QRS Duration, and No Dyssynchrony," *Circulation*, Oct. 27, 2009; 120: 1687-1694.

(PCT/US2019/019933) PCT Notification of Transmittal of the International Search Report and the Written Opinion of the International Searching Authority, dated May 20, 2019, 13 pages.

\* cited by examiner

DELIVERY OF PACING THERAPY BY A CARDIAC PACING DEVICE

The disclosure herein relates delivery of a pacing therapy by a cardiac pacing device, and particularly to systems and methods for evaluation and adjustment of delivery of a pacing therapy by a cardiac pacing device.

SUMMARY

The exemplary system, device and methods described herein involve the combined use of an electrocardiogram (ECG) belt and an implantable medical device to deliver a pacing therapy, such as closed loop cardiac resynchronization therapy. In one example, the medical device system may include the combined use of an ECG belt and a pacing device. The pacing device may include an implantable cardiac device (ICD) having a patient activity sensor, such as an accelerometer, coupled to a housing of the ICD. In another example, the pacing device may be a leadless pacing device that includes atrial sensing capabilities from a patient activity sensor, such as an accelerometer, integrated within the device. In another example, the pacing device may include a combination of a leadless pacing device having an accelerometer and an extravascular device capable of sensing P-waves and transmitting a trigger signal to the leadless pacing device to instruct the pacing device to deliver pacing therapy using a predetermined pacing parameter setting, such as a pre-determined atrioventricular (AV) delay, for example. In another example, the implantable medical device system may include the combined use of the ECG belt and an implantable pacemaker, cardioverter, and/or defibrillator, that delivers, or provides, electrical signals (e.g., paces, etc.) to and/or senses electrical signals from the heart 12 of the patient 14 via electrodes coupled to one or more of the leads 18, 20, 22 and introduced transveneously to the heart.

In either example, a pacing parameter associated with the delivered pacing therapy that produces an optimal synchronization pattern for a specific patient, such as an AV delay, may be determined based on electrical heterogeneity metrics determined using the ECG belt during placement of the pacing device. The placement of the pacing device by the physician within the patient may be guided based on optimal electrical activation from the ECG belt determined using electrical heterogeneity metrics, such as a left ventricular activation time (LVAT) and a standard deviation of activation times (SDAT).

Once positioning of the pacing device within the patient is completed, an optimal setting for a pacing parameter may be determined based on the lowest electrical heterogeneity metrics, and the corresponding optimal electro-mechanical (EM) response interval between the pacing event and the mechanical response determined from the pacing device may be defined. The mechanical response may be measured at the peak of an accelerometer signal, for example, within a pre-defined timing window (e.g. 250 ms) following a pacing event of the leadless pacing device.

Under ambulatory conditions, the pacing device may subsequently monitor this EM interval response and maintain the same optimal interval by adjusting one or more pacing parameter settings. In an example where the pacing parameter is an AV delay, determining that the mechanical response occurs too soon after pacing may indicate that pacing is being delivered at a longer AV delay than optimal, potentially causing pseudo-fusion or ineffective pacing. Therefore, the device may shorten the AV delay to bring the electro-mechanical response interval back to the optimal value. On the other hand, determining that the mechanical response occurs too late after pacing may indicate that pacing is being delivered at a shorter AV delay than is optimal, leading to slower cell-to-cell conduction and delayed activation, and resulting in a delayed mechanical response. Therefore, the pacing device may prolong the AV delay to promote more fusion of intrinsic rhythm and bring the pacing interval back to the optimal value.

In another example, the pacing device may increase the pacing rate during atrial tachyarrhythmias/atrial fibrillation in response to determining that the electro-mechanical response interval is too short (intrinsic conduction coming in too early), or the pacing device may decrease the pacing rate during atrial tachyarrhythmias/atrial fibrillation in response to determining that the electro-mechanical response interval is too long (no fusion from intrinsic conduction).

In one example, a method of delivering a cardiac pacing therapy, comprising: delivering a non-ambulatory pacing therapy from a pacing device; sensing electrical activity of tissue of a patient from a plurality of external electrodes during the delivered non-ambulatory pacing therapy; determining an optimal electro-mechanical (EM) response time in response to the sensed electrical activity; delivering an ambulatory pacing therapy from the pacing device; sensing an EM signal from an EM sensor of the pacing device; determining a current EM response time in response to the sensed EM signal; comparing the current EM response time to the optimal EM response time; and adjusting a pacing parameter setting of the ambulatory pacing therapy in response to the comparing.

In one example, an implantable medical device system for delivering a pacing therapy, comprising: a pacing device comprising: one or more electrodes for sensing cardiac signals and delivering the pacing therapy, the pacing therapy comprising one of a non-ambulatory pacing therapy and an ambulatory pacing therapy; a processor configured to configured to control delivery of the pacing therapy via the one or more electrodes,; and an electromechanical (EM) sensor to sense an EM signal of the patient in response to the delivered pacing therapy; a plurality of external electrodes capable of being positioned along a torso of a patient to sense electrical activity of tissue of the patient; and a computing apparatus electrically coupled to the plurality of external electrodes, wherein the computing apparatus is configured to determine an optimal electromechanical (EM) response time in response to the sensed electrical activity from the plurality of external electrodes during delivery of non-ambulatory pacing therapy by the pacing device, and wherein the processor of the pacing device is further configured to sense an EM signal from the EM sensor during delivery of ambulatory pacing, determine a current EM response time in response to the sensed EM signal, compare the current EM response time determined by the processor of the pacing device during delivery of ambulatory pacing to the optimal EM response time determined by the computing apparatus during delivery of non-ambulatory pacing therapy by the pacing device, and adjust a pacing parameter setting for delivering the ambulatory pacing therapy in response to the comparing.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1:
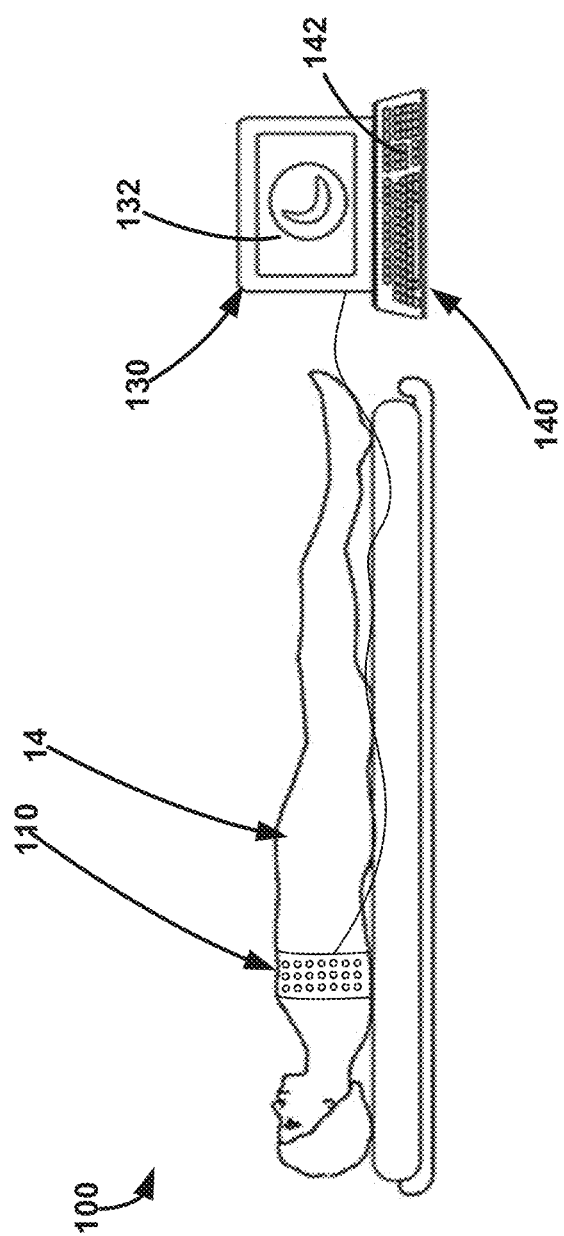
FIG. 1 is a diagram of an exemplary system including electrode apparatus, display apparatus, and computing apparatus.

In the following detailed description of illustrative embodiments, reference is made to the accompanying figures of the drawing which form a part hereof, and in which are shown, by way of illustration, specific embodiments which may be practiced. It is to be understood that other embodiments may be utilized, and structural changes may be made without departing from (e.g., still falling within) the scope of the disclosure presented hereby.

Exemplary systems and methods shall be described with reference to FIGS. 1-10. It will be apparent to one skilled in the art that elements or processes from one embodiment may be used in combination with elements or processes of the other embodiments, and that the possible embodiments of such methods and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

The exemplary system, device and methods described herein involve the combined use of an electrocardiogram (ECG) belt and an implantable medical device to deliver a pacing therapy, such as closed loop cardiac resynchronization therapy. In one example, the medical device system may include the combined use of an ECG belt and a pacing device. The pacing device may include an implantable cardiac device (ICD) having a patient activity sensor, such as an accelerometer, coupled to a housing of the ICD. In another example, the pacing device may be a leadless pacing device that includes atrial sensing capabilities from a patient activity sensor, such as an accelerometer, integrated within the device. In another example, the pacing device may include a combination of a leadless pacing device having an accelerometer and an extravascular device capable of sensing P-waves and transmitting a trigger signal to the leadless pacing device to instruct the pacing device to deliver pacing therapy using a predetermined pacing parameter setting, such as a pre-determined atrioventricular (AV) delay, for example. In another example, the implantable medical device system may include the combined use of the ECG belt and an implantable pacemaker, cardioverter, and/or defibrillator, that delivers, or provides, electrical signals (e.g., paces, etc.) to and/or senses electrical signals from the heart 12 of the patient 14 via electrodes coupled to one or more of the leads 18, 20, 22 and introduced transveneously to the heart.

In either example, a pacing parameter associated with the delivered pacing therapy that produces an optimal synchronization pattern for a specific patient, such as an AV delay, may be determined based on electrical heterogeneity metrics determined using the ECG belt during placement of the pacing device. The placement of the pacing device by the physician within the patient may be guided based on optimal electrical activation from the ECG belt determined using electrical heterogeneity metrics, such as a left ventricular activation time (LVAT) and a standard deviation of activation times (SDAT).

Once positioning of the pacing device within the patient is completed, an optimal setting for a pacing parameter may be determined based on the lowest electrical heterogeneity metrics, and the corresponding optimal electro-mechanical (EM) response interval between the pacing event and the mechanical response determined from the pacing device may be defined. The mechanical response may be measured at the peak of an accelerometer signal, for example, within a pre-defined timing window (e.g. 250 ms) following a pacing event of the leadless pacing device.

Under ambulatory conditions, the pacing device may subsequently monitor this EM interval response and maintain the same optimal interval by adjusting one or more pacing parameter settings. In an example where the pacing parameter is an AV delay, determining that the mechanical response occurs too soon after pacing may indicate that pacing is being delivered at a longer AV delay than optimal, potentially causing pseudo-fusion or ineffective pacing. Therefore, the device may shorten the AV delay to bring the electro-mechanical response interval back to the optimal value. On the other hand, determining that the mechanical response occurs too late after pacing may indicate that pacing is being delivered at a shorter AV delay than is optimal, leading to slower cell-to-cell conduction and delayed activation, and resulting in a delayed mechanical response. Therefore, the pacing device may prolong the AV delay to promote more fusion of intrinsic rhythm and bring the pacing interval back to the optimal value.

In another example, the pacing device may increase the pacing rate during atrial tachyarrhythmias/atrial fibrillation in response to determining that the electro-mechanical response interval is too short (intrinsic conduction coming in too early), or the pacing device may decrease the pacing rate during atrial tachyarrhythmias/atrial fibrillation in response to determining that the electro-mechanical response interval is too long (no fusion from intrinsic conduction).

FIG. 1 is a schematic diagram of an exemplary implantable medical device system for delivering a pacing therapy according to the present disclosure. As illustrated in FIG. 1, an implantable medical device system 100 may include an electrode apparatus 110, a display apparatus 130, a computing apparatus 140, and a pacing device (not shown in FIG. 1), described below, capable of being positioned within a patient 14. The electrode apparatus 110 as shown includes a plurality of electrodes incorporated, or included, within a band wrapped around the chest, or torso, of the patient 14. The electrode apparatus 110 is operatively coupled to the computing apparatus 140 (e.g., through one or wired electrical connections, wirelessly, etc.) to provide electrical signals from each of the electrodes to the computing apparatus 140 for analysis, evaluation, etc. Exemplary electrode apparatus may be described in U.S. Pat. No. 9,320,446 entitled "Bioelectric Sensor Device and Methods" and issued on Apr. 26, 2016, which is incorporated herein by reference in its entirety. Further, exemplary electrode apparatus 110 will be described in more detail in reference to FIGS. 2-3.

Although not described herein, the exemplary system 100 may further include imaging apparatus. The imaging apparatus may be any type of imaging apparatus configured to image, or provide images of, at least a portion of the patient in a noninvasive manner. For example, the imaging apparatus may not use any components or parts that may be located within the patient to provide images of the patient except noninvasive tools such as contrast solution. It is to be understood that the exemplary systems, methods, and interfaces described herein may further use imaging apparatus to provide noninvasive assistance to a user (e.g., a physician) to locate or select a pacing electrode or pacing vector proximate the patient's heart for pacing therapy in conjunction with the evaluation of pacing therapy.

For example, the exemplary systems, methods, and interfaces may provide image guided navigation that may be used to navigate leads including electrodes, leadless electrodes, wireless electrodes, catheters, etc., within the patient's body while also providing noninvasive cardiac therapy evaluation including determining whether a paced setting is acceptable or determining whether one or more selected parameters are acceptable, such as selected location information (e.g., location information for the electrodes to target the His bundle). Exemplary systems and methods that use imaging apparatus and/or electrode apparatus may be described in U.S. Patent Publication No. 2014/0371832 filed on Jun. 12, 2013 and entitled "Implantable Electrode Location Selection," U.S. Patent Publication No. 2014/0371833 filed on Jun. 12, 2013 and entitled "Implantable Electrode Location Selection," U.S. Patent Publication No. 2014/0323892 filed on Mar. 27, 2014 and entitled "Systems, Methods, and Interfaces for Identifying Effective Electrodes," U.S. Patent Publication No. 2014/0323882 filed on Mar. 27, 2014 and entitled "Systems, Methods, and Interfaces for Identifying Optical Electrical Vectors," each of which is incorporated herein by reference in its entirety. Further exemplary His bundle pacing may be described in U.S. Pat. No. 6,937,897 issued on Aug. 30, 2005 and entitled "Electrode for His bundle stimulation," and U.S. Pat. No. 7,027,876 issued on Apr. 11, 2006 and entitled "Lead system for providing electrical stimulation to the Bundle of His," each of which is incorporated herein by reference in its entirety.

Exemplary imaging apparatus may be configured to capture x-ray images and/or any other alternative imaging modality. For example, the imaging apparatus may be configured to capture images, or image data, using isocentric fluoroscopy, bi-plane fluoroscopy, ultrasound, computed tomography (CT), multi-slice computed tomography (MSCT), magnetic resonance imaging (MRI), high frequency ultrasound (HIFU), optical coherence tomography (OCT), intra-vascular ultrasound (IVUS), two dimensional (2D) ultrasound, three dimensional (3D) ultrasound, four dimensional (4D) ultrasound, intraoperative CT, intraoperative MlII, etc. Further, it is to be understood that the imaging apparatus may be configured to capture a plurality of consecutive images (e.g., continuously) to provide video frame data. In other words, a plurality of images taken over time using the imaging apparatus may provide video frame, or motion picture, data. Additionally, the images may also be obtained and displayed in two, three, or four dimensions. In more advanced forms, four-dimensional surface rendering of the heart or other regions of the body may also be achieved by incorporating heart data or other soft tissue data from a map or from pre-operative image data captured by MRI, CT, or echocardiography modalities. Image datasets from hybrid modalities, such as positron emission tomography (PET) combined with CT, or single photon emission computer tomography (SPECT) combined with CT, could also provide functional image data superimposed onto anatomical data, e.g., to be used to navigate treatment apparatus proximate target location for placing electrodes within specific areas of interest in the heart.

Systems and/or imaging apparatus that may be used in conjunction with the exemplary systems and method described herein are described in U.S. Pat. App. Pub. No. 2005/0008210 to Evron et al. published on Jan. 13, 2005, U.S. Pat. App. Pub. No. 2006/0074285 to Zarkh et al. published on Apr. 6, 2006, U.S. Pat. App. Pub. No. 2011/0112398 to Zarkh et al. published on May 12, 2011, U.S. Pat. App. Pub. No. 2013/0116739 to Brada et al. published on May 9, 2013, U.S. Pat. No. 6,980,675 to Evron et al. issued on Dec. 27, 2005, U.S. Pat. No. 7,286,866 to Okerlund et al. issued on Oct. 23, 2007, U.S. Pat. No. 7,308,297 to Reddy et al. issued on Dec. 11, 2011, U.S. Pat. No. 7,308,299 to Burrell et al. issued on Dec. 11, 2011, U.S. Pat. No. 7,321,677 to Evron et al. issued on Jan. 22, 2008, U.S. Pat. No. 7,346,381 to Okerlund et al. issued on Mar. 18, 2008, U.S. Pat. No. 7,454,248 to Burrell et al. issued on Nov. 18, 2008, U.S. Pat. No. 7,499,743 to Vass et al. issued on Mar. 3, 2009, U.S. Pat. No. 7,565,190 to Okerlund et al. issued on Jul. 21, 2009, U.S. Pat. No. 7,587,074 to Zarkh et al. issued on Sep. 8, 2009, U.S. Pat. No. 7,599,730 to Hunter et al. issued on Oct. 6, 2009, U.S. Pat. No. 7,613,500 to Vass et al. issued on Nov. 3, 2009, U.S. Pat. No. 7,742,629 to Zarkh et al. issued on Jun. 22, 2010, U.S. Pat. No. 7,747,047 to Okerlund et al. issued on Jun. 29, 2010, U.S. Pat. No. 7,778,685 to Evron et al. issued on Aug. 17, 2010, U.S. Pat. No. 7,778,686 to Vass et al. issued on Aug. 17, 2010, U.S. Pat. No. 7,813,785 to Okerlund et al. issued on Oct. 12, 2010, U.S. Pat. No. 7,996,063 to Vass et al. issued on Aug. 9, 2011, U.S. Pat. No. 8,060,185 to Hunter et al. issued on Nov. 15, 2011, and U.S. Pat. No. 8,401,616 to Verard et al. issued on Mar. 19, 2013, each of which is incorporated herein by reference in its entirety.

The display apparatus 130 and the computing apparatus 140 may be configured to display and analyze data such as, e.g., electrical signals (e.g., electrocardiogram data), cardiac information representative of at least one of mechanical cardiac functionality and electrical cardiac functionality, etc. Cardiac information may include, e.g., electrical heterogeneity information or electrical dyssynchrony information, surrogate electrical activation information or data, etc. that is generated using electrical signals gathered, monitored, or collected, using the electrode apparatus 110. In at least one embodiment, the computing apparatus 140 may be a server, a personal computer, or a tablet computer. The computing apparatus 140 may be configured to receive input from input apparatus 142 and transmit output to the display apparatus 130. Further, the computing apparatus 140 may include data storage that may allow for access to processing programs or routines and/or one or more other types of data, e.g., for driving a graphical user interface configured to noninvasively assist a user in evaluating a pacing location (e.g., the location of an implantable electrode used for pacing, the location of pacing therapy delivered by a particular pacing vector, etc.).

The computing apparatus 140 may be operatively coupled to the input apparatus 142 and the display apparatus 130 to, e.g., transmit data to and from each of the input apparatus 142 and the display apparatus 130. For example, the computing apparatus 140 may be electrically coupled to each of the input apparatus 142 and the display apparatus 130 using, e.g., analog electrical connections, digital electrical connections, wireless connections, bus-based connections, network-based connections, internet-based connections, etc. As described further herein, a user may provide input to the input apparatus 142 to manipulate, or modify, one or more graphical depictions displayed on the display apparatus 130 and to view and/or select one or more pieces of information related to the cardiac therapy.

Although as depicted the input apparatus 142 is a keyboard, it is to be understood that the input apparatus 142 may include any apparatus capable of providing input to the computing apparatus 140 to perform the functionality, methods, and/or logic described herein. For example, the input apparatus 142 may include a mouse, a trackball, a touchscreen (e.g., capacitive touchscreen, a resistive touchscreen, a multi-touch touchscreen, etc.), etc. Likewise, the display apparatus 130 may include any apparatus capable of displaying information to a user, such as a graphical user interface 132 including cardiac information, textual instructions, graphical depictions of electrical activation information, graphical depictions of anatomy of a human heart, images or graphical depictions of the patient's heart, graphical depictions of locations of one or more electrodes, graphical depictions of a human torso, images or graphical depictions of the patient's torso, graphical depictions or actual images of implanted electrodes and/or leads, etc. Further, the display apparatus 130 may include a liquid crystal display, an organic light-emitting diode screen, a touchscreen, a cathode ray tube display, etc.

The processing programs or routines stored and/or executed by the computing apparatus 140 may include programs or routines for computational mathematics, matrix mathematics, dispersion determinations (e.g. standard deviations, variances, ranges, interquartile ranges, mean absolute differences, average absolute deviations, etc.), filtering algorithms, maximum value determinations, minimum value determinations, threshold determinations, moving windowing algorithms, decomposition algorithms, compression algorithms (e.g., data compression algorithms), calibration algorithms, image construction algorithms, signal processing algorithms (e.g., various filtering algorithms, Fourier transforms, fast Fourier transforms, etc.), standardization algorithms, comparison algorithms, vector mathematics, or any other processing required to implement one or more exemplary methods and/or processes described herein. Data stored and/or used by the computing apparatus 140 may include, for example, electrical signal/waveform data from the electrode apparatus 110, dispersions signals, windowed dispersions signals, parts or portions of various signals, electrical activation times from the electrode apparatus 110, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein (e.g., electrical signals, cardiac information, etc.), or any other data that may be necessary for carrying out the one and/or more processes or methods described herein.

In one or more embodiments, the exemplary systems, methods, and interfaces may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The one or more programs used to implement the systems, methods, and/or interfaces described herein may be provided using any programmable language, e.g., a high-level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the exemplary systems, methods, and/or interfaces may be implemented using a computer readable storage medium, configured with a computer program, where the storage medium so configured causes the computer to operate in a specific and predefined manner to perform functions described herein. Further, in at least one embodiment, the exemplary systems, methods, and/or interfaces may be described as being implemented by logic (e.g., object code) encoded in one or more non-transitory media that includes code for execution and, when executed by a processor, is operable to perform operations such as the methods, processes, and/or functionality described herein.

The computing apparatus 140 may be, for example, any fixed or mobile computer system (e.g., a controller, a microcontroller, a personal computer, minicomputer, tablet computer, etc.) and may be generally described as including processing circuitry. The exact configuration of the computing apparatus 140 is not limiting, and essentially any device capable of providing suitable computing capabilities and control capabilities (e.g., graphics processing, etc.) may be used. As described herein, a digital file may be any medium (e.g., volatile or non-volatile memory, a CD-ROM, a punch card, magnetic recordable medium such as a disk or tape, etc.) containing digital bits (e.g., encoded in binary, trinary, etc.) that may be readable and/or writeable by computing apparatus 140 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

Figure 2:
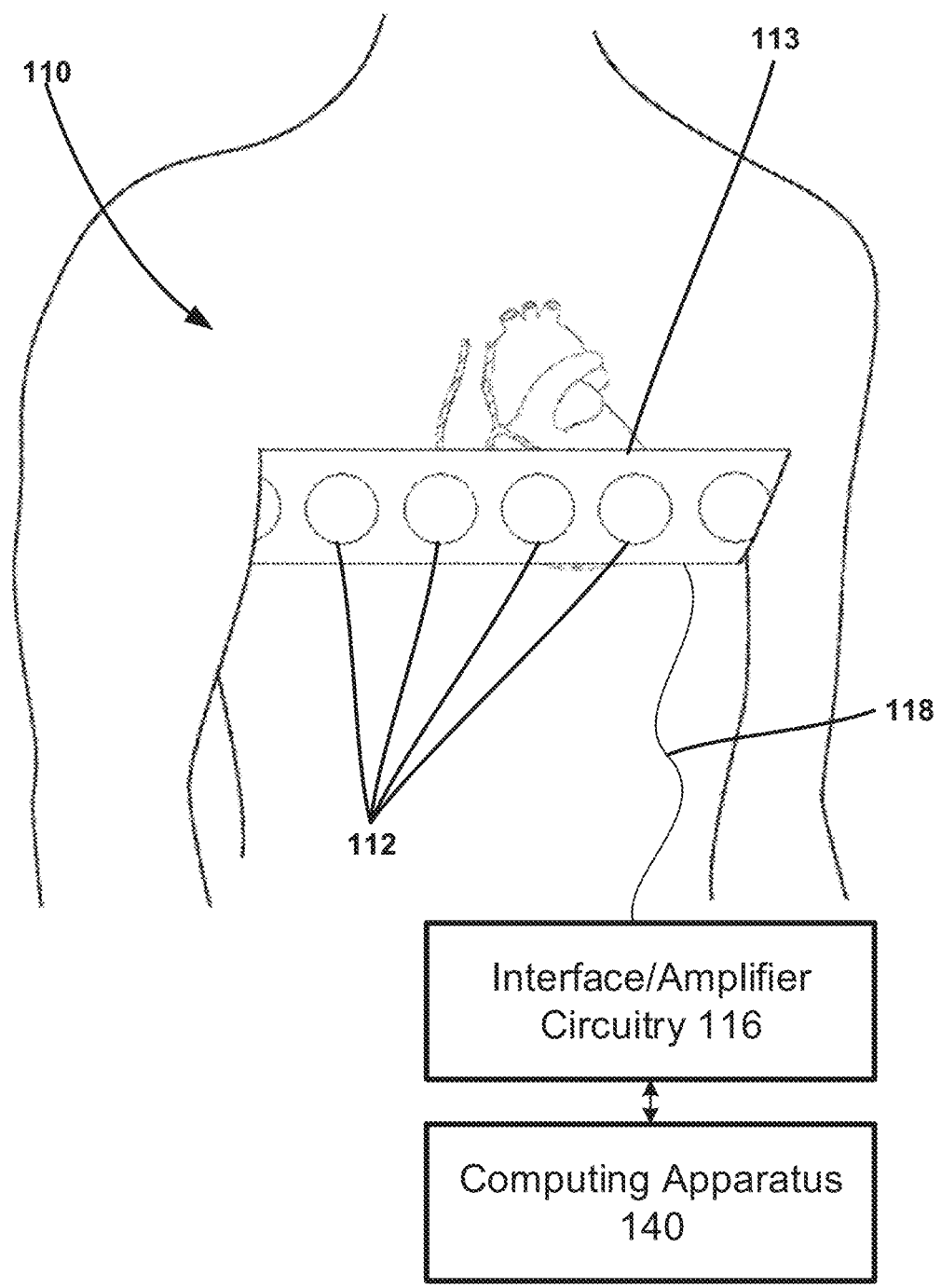
FIGS. 2-3 are diagrams of exemplary external electrode apparatus for measuring torso-surface potentials.

Electrical activation times of the patient's heart may be useful to evaluate a patient's cardiac condition and/or cardiac pacing therapy being delivered to a patient. Surrogate electrical activation information or data of one or more regions of a patient's heart may be monitored, or determined, using electrode apparatus 110 as shown in FIG. 1 and in FIG. 2-3. The exemplary electrode apparatus 110 may be configured to measure body-surface potentials of a patient 14 and, more particularly, torso-surface potentials of a patient 14. As shown in FIG. 2, the exemplary electrode apparatus 110 may include a set, or array, of electrodes 112, a strap 113, and interface/amplifier circuitry 116. The electrodes 112 may be attached, or coupled, to the strap 113 and the strap 113 may be configured to be wrapped around the torso of a patient 14 such that the electrodes 112 surround the patient's heart. As further illustrated, the electrodes 112 may be positioned around the circumference of a patient 14, including the posterior, lateral, posterolateral, anterolateral, and anterior locations of the torso of a patient 14.

Further, the electrodes 112 may be electrically connected to interface/amplifier circuitry 116 via wired connection 118. The interface/amplifier circuitry 116 may be configured to amplify the signals from the electrodes 112 and provide the signals to the computing apparatus 140. Other exemplary systems may use a wireless connection to transmit the signals sensed by electrodes 112 to the interface/amplifier circuitry 116 and, in turn, the computing apparatus 140, e.g., as channels of data. For example, the interface/amplifier circuitry 116 may be electrically coupled to each of the computing apparatus 140 and the display apparatus 130 using, e.g., analog electrical connections, digital electrical connections, wireless connections, bus-based connections, network-based connections, internet-based connections, etc.

Although in the example of FIG. 2 the electrode apparatus 110 includes a strap 113, in other examples any of a variety of mechanisms, e.g., tape or adhesives, may be employed to aid in the spacing and placement of electrodes 112. In some examples, the strap 113 may include an elastic band, strip of tape, or cloth. In other examples, the electrodes 112 may be placed individually on the torso of a patient 14. Further, in other examples, electrodes 112 (e.g., arranged in an array) may be part of, or located within, patches, vests, and/or other manners of securing the electrodes 112 to the torso of the patient 14.

The electrodes 112 may be configured to surround the heart of the patient 14 and record, or monitor, the electrical signals associated with the depolarization and repolarization of the heart after the signals have propagated through the torso of a patient 14. Each of the electrodes 112 may be used in a unipolar configuration to sense the torso-surface potentials that reflect the cardiac signals. The interface/amplifier circuitry 116 may also be coupled to a return or indifferent electrode (not shown) that may be used in combination with each electrode 112 for unipolar sensing. In some examples, there may be about 12 to about 50 electrodes 112 spatially distributed around the torso of patient. Other configurations may have more or fewer electrodes 112.

The computing apparatus 140 may record and analyze the electrical activity (e.g., torso-surface potential signals) sensed by electrodes 112 and amplified/conditioned by the interface/amplifier circuitry 116. The computing apparatus 140 may be configured to analyze the signals from the electrodes 112 to provide as anterior and posterior electrode signals and surrogate cardiac electrical activation times, e.g., representative of actual, or local, electrical activation times of one or more regions of the patient's heart as will be further described herein. Further, the electrical signals measured at the left anterior surface location of a patient's torso may be representative, or surrogates, of electrical signals of the left anterior left ventricle region of the patient's heart, electrical signals measured at the left lateral surface location of a patient's torso may be representative, or surrogates, of electrical signals of the left lateral left ventricle region of the patient's heart, electrical signals measured at the left posterolateral surface location of a patient's torso may be representative, or surrogates, of electrical signals of the posterolateral left ventricle region of the patient's heart, and electrical signals measured at the posterior surface location of a patient's torso may be representative, or surrogates, of electrical signals of the posterior left ventricle region of the patient's heart. In one or more embodiments, measurement of activation times can be performed by measuring the period of time between an onset of cardiac depolarization (e.g., onset of QRS complex) and an appropriate fiducial point such as, e.g., a peak value, a minimum value, a minimum slope, a maximum slope, a zero crossing, a threshold crossing, etc.

Additionally, the computing apparatus 140 may be configured to provide graphical user interfaces depicting the surrogate electrical activation times obtained using the electrode apparatus 110. Exemplary systems, methods, and/or interfaces may noninvasively use the electrical information collected using the electrode apparatus 110 to evaluate a patient's cardiac condition and/or pacing therapy being delivered to the patient.

Figure 3:
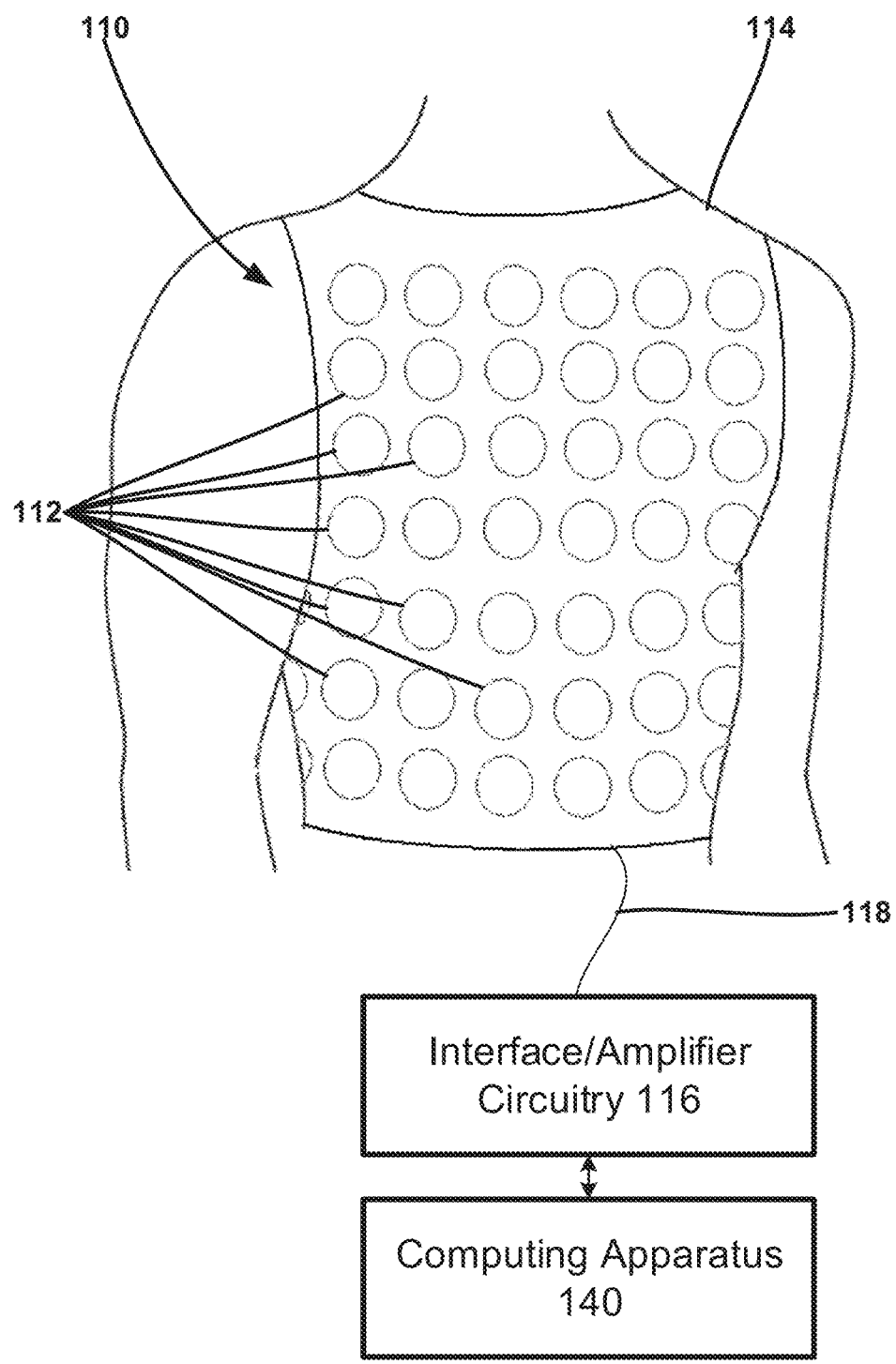

FIG. 3 illustrates another exemplary electrode apparatus 110 that includes a plurality of electrodes 112 configured to surround the heart of the patient 14 and record, or monitor, the electrical signals associated with the depolarization and repolarization of the heart after the signals have propagated through the torso of the patient 14. The electrode apparatus 110 may include a vest 114 upon which the plurality of electrodes 112 may be attached, or to which the electrodes 112 may be coupled. In at least one embodiment, the plurality, or array, of electrodes 112 may be used to collect electrical information such as, e.g., surrogate electrical activation times. Similar to the electrode apparatus 110 of FIG. 2, the electrode apparatus 110 of FIG. 3 may include interface/amplifier circuitry 116 electrically coupled to each of the electrodes 112 through a wired connection 118 and be configured to transmit signals from the electrodes 112 to the computing apparatus 140. As illustrated, the electrodes 112 may be distributed over the torso of a patient 14, including, for example, the anterior, lateral, posterolateral, anterolateral, and posterior surfaces of the torso of the patient 14.

The vest 114 may be formed of fabric with the electrodes 112 attached to the fabric. The vest 114 may be configured to maintain the position and spacing of electrodes 112 on the torso of the patient 14. Further, the vest 114 may be marked to assist in determining the location of the electrodes 112 on the surface of the torso of the patient 14. In one or more embodiments, the vest 114 may include 17 or more anterior electrodes positionable proximate the anterior torso of the patient, and 39 or more posterior electrodes positionable proximate the anterior torso of the patient. In some examples, there may be about 25 electrodes 112 to about 256 electrodes 112 distributed around the torso of the patient 14, though other configurations may have more or less electrodes 112.

As described herein, the electrode apparatus 110 may be configured to measure electrical information (e.g., electrical signals) representing different regions of a patient's heart. For example, activation times of different regions of a patient's heart can be approximated from surface electrocardiogram (ECG) activation times measured using surface electrodes in proximity to surface areas corresponding to the different regions of the patient's heart.

The exemplary systems, methods, and interfaces may be used to provide noninvasive assistance to a user in the evaluation of a cardiac pacing therapy by use of the electrode apparatus 110 (e.g., cardiac therapy being presently-delivered to a patient during implantation or after implantation). Further, the exemplary systems, methods, and interfaces may be used to assist a user in the configuration of the cardiac therapy being delivered to a patient.

Figure 4:
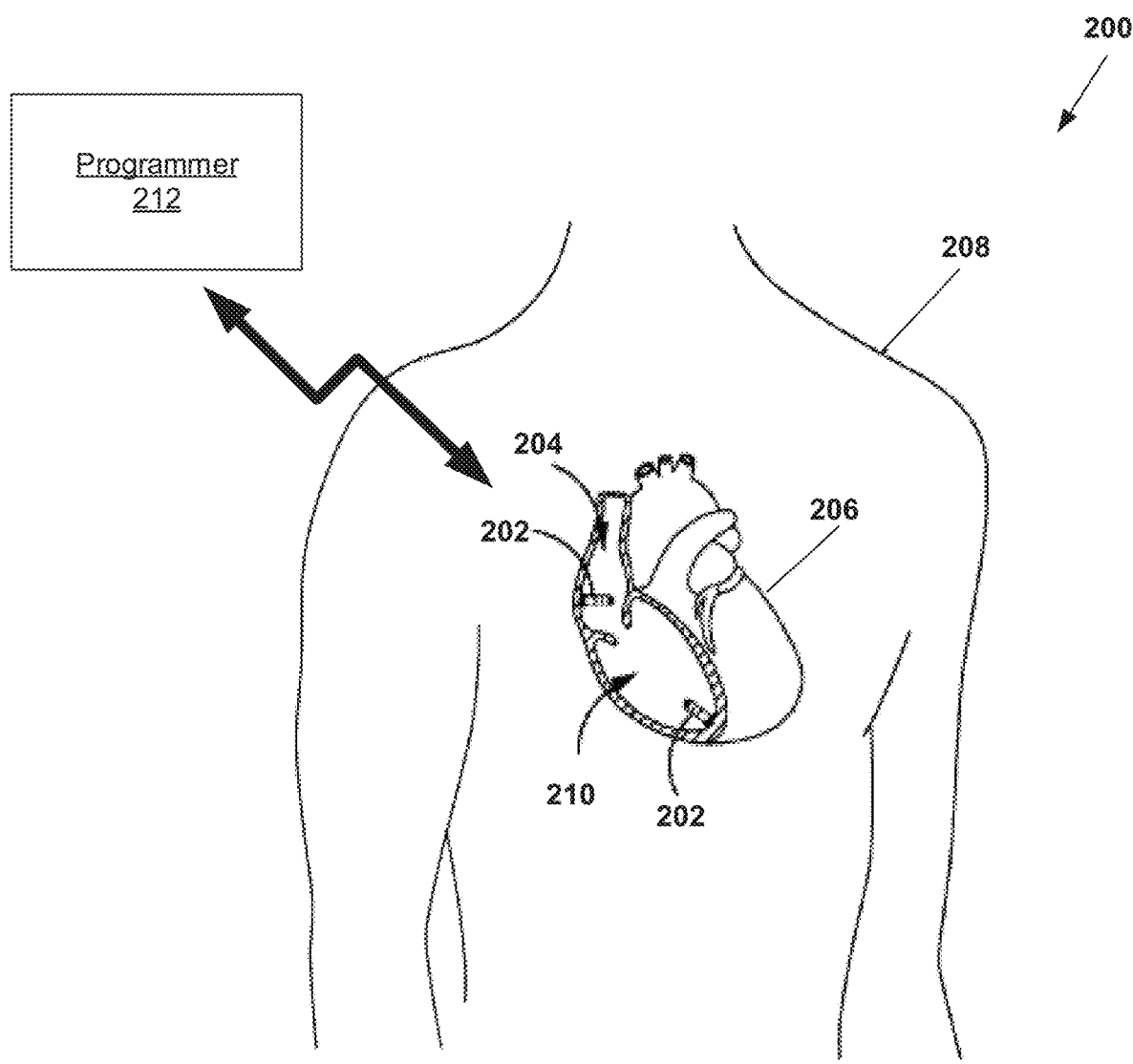
FIG. 4 is a schematic diagram illustrating an example medical device system for delivering a therapeutic agent, consistent with an example of the present disclosure.

FIG. 4 is a schematic diagram illustrating an example pacing device of a medical device system for delivering a pacing therapy, consistent with an example of the present disclosure. As illustrated in FIG. 4, a system 200 for use in evaluation and delivery of pacing therapy according to the present disclosure may include one or more leadless pacemaker device 202 configured to be positioned within either a right atrium 204 of a heart 206 of a patient 208, within a right ventricle 210 of the patient 208, or both, as illustrated in FIG. 4. The leadless pacemaker device 202 may be configured to monitor electrical activity of the patient's 208 heart 206 and/or provide electrical therapy to the heart 206.

Figure 5:
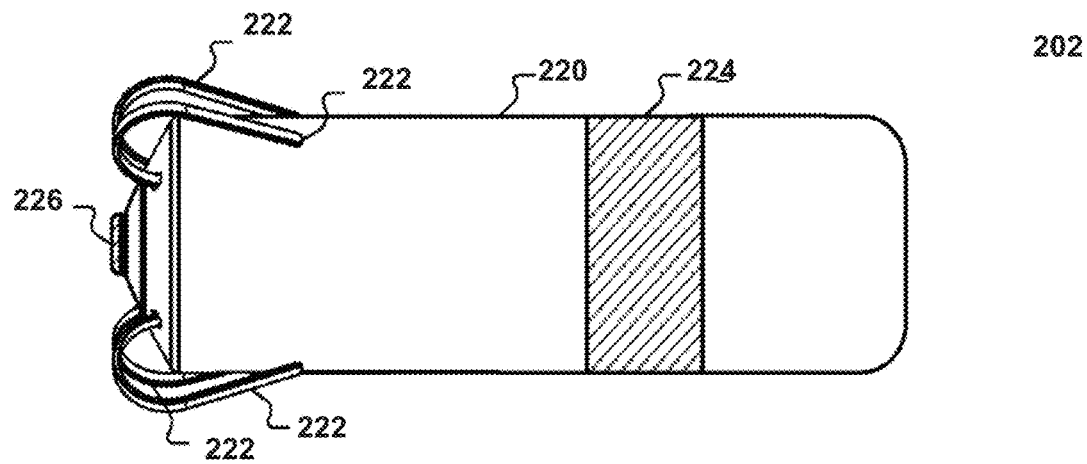
FIG. 5 is a conceptual diagram illustrating the example medical device of FIG. 4 according to an example of the present disclosure.

FIG. 5 is a conceptual diagram illustrating the example pacing device of FIG. 4 according to an example of the present disclosure. As illustrated in FIG. 5, the leadless pacemaker device 202 a housing 220, fixation tines 222, a proximal electrode 224 and a distal electrode 226. The housing 220 may have a pill-shaped cylindrical form factor in some examples. The fixation tines 222 are configured to connect (e.g., anchor) device 202 to heart 206, and may be fabricated from a shape memory material, such as Nitinol. In some examples, the fixation tines 222 may connect one or both leadless pacemaker device 202 to the heart 206 within one or both of the chambers 204, 210 of the heart 206, as illustrated in FIG. 4. In another example, the fixation tines 222 may be configured to anchor a single leadless pacemaker device 202 to the heart 206 within only the right atrium 204. Although the leadless pacemaker device 202 includes a plurality of fixation tines 222 that are configured to anchor the leadless pacemaker device 202 to cardiac tissue in the right atrium 204, the left atrium 210, or both, it is contemplated that a leadless device according to the present disclosure may be fixed to cardiac tissue using other types of fixation mechanisms.

The leadless pacemaker device 202 may include one or more electrodes for sensing electrical activity of the heart 206 and/or delivering electrical stimulation to the heart 206. While the leadless pacemaker device 202 shown includes two electrodes 224, 226, more than two electrodes may be included on the leadless pacemaker device 202 in other examples. Electrode 226 may be referred to as a "tip electrode," and electrode 224 may be referred to as a "ring electrode." The fixation tines 222 may anchor the leadless pacemaker device 202 to cardiac tissue such that the tip electrode 226 maintains contact with the cardiac tissue. The ring electrode 224 may be located on the housing 220. For example, the ring electrode 224 may be a cylindrical electrode that wraps around the housing 220. Although the ring electrode 224 is illustrated as being a cylindrical electrode that wraps around the housing 220, the ring electrode 224 may include other geometries. In some examples, the housing 220 may be formed from a conductive material. In these examples, the housing 220 may act as an electrode of the leadless pacemaker device 202.

The housing 220 houses electronic components of the leadless pacemaker device 202. Electronic components may include any discrete and/or integrated electronic circuit components that implement analog and/or digital circuits capable of producing the functions attributed to the leadless pacemaker device 202 described herein. For example, the housing 220 may house electronic components that sense electrical activity via electrodes 224, 226 and/or deliver electrical stimulation via electrodes 224, 226. Additionally, the housing 220 may also include memory that includes instructions that, when executed by one or more processing circuits housed within the housing 220, cause the leadless pacemaker device 202 to perform various functions attributed to the leadless pacemaker device 202 herein. The housing 220 may also house sensors that sense physiological conditions of the patient 208, such as an accelerometer and/or a pressure sensor.

In some examples, the housing 220 may house a communication module that enables the leadless pacemaker device 202 to communicate with other electronic devices, such as a programmer 212 or other external patient monitor. In some examples, the housing 220 may house an antenna for wireless communication. The housing 220 may also include a power source, such as a battery. Electronic components included within the housing 220 are described in further detail hereinafter.

Figure 6:
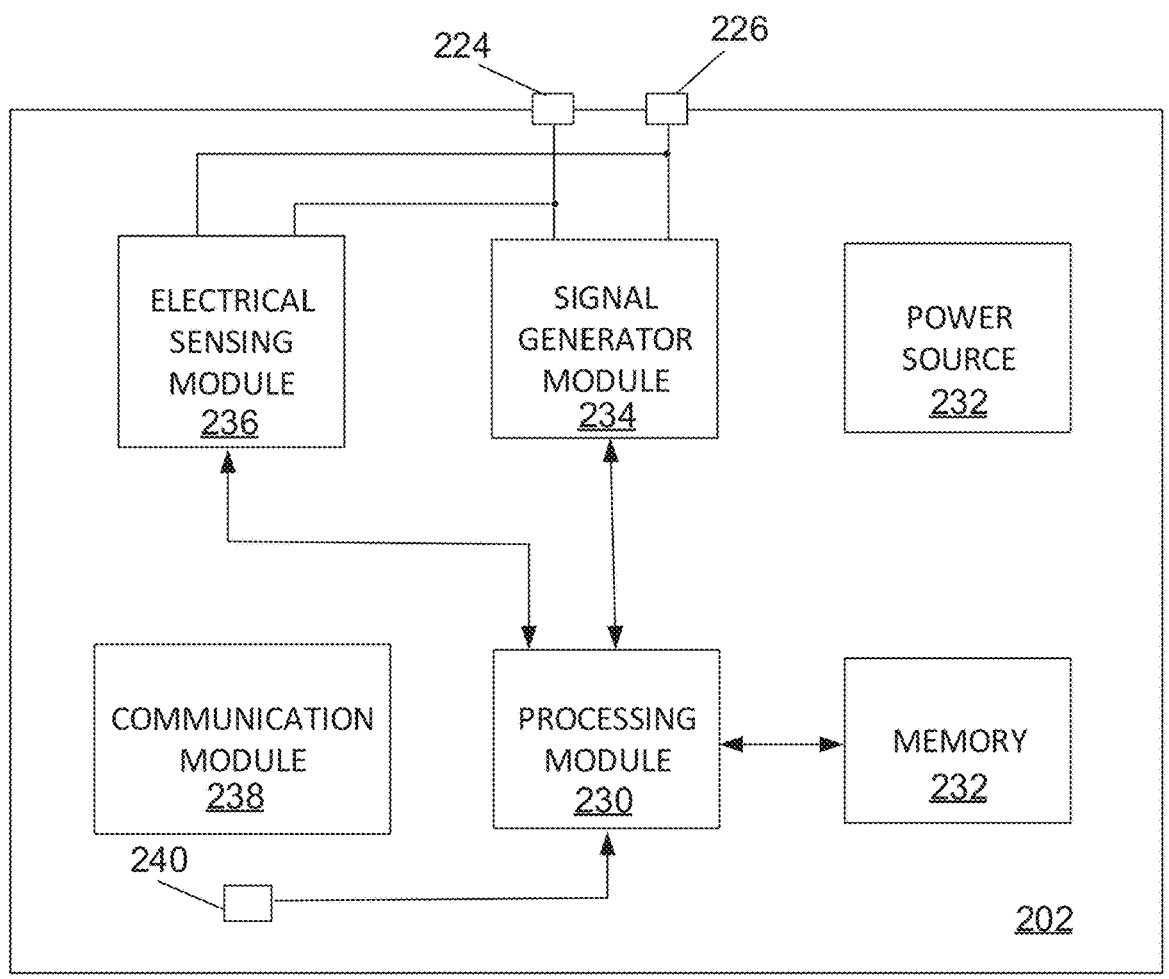
FIG. 6 is a functional block diagram of an example leadless pacemaker device according to an example of the present disclosure.

FIG. 6 is a functional block diagram of an example leadless pacemaker device according to an example of the present disclosure. As illustrated in FIG. 6, a pacing therapy delivery system utilized in the delivery of pacing therapy according to the present disclosure may include a leadless pacemaker device 202 positioned in the atrium 204 of the heart 206, a leadless pacemaker device 202 positioned within the ventricle 210 of the heart 206, or a leadless pacemaker 202 positioned in both the atrium 204 of the heart 206 and the ventricle 210 of the heart 206. In addition, the system may include a programmer 212 used to program one or both leadless pacemaker device 202 and/or to retrieve data from one or both leadless pacemaker device 202. Each leadless pacemaker device 202 may include a processing module 230, memory 232 a signal generator module 234, an electrical sensing module 236, a communication module 238, a sensor 240, and a power source 242. The power source 242 may include a battery, e.g., a rechargeable or non-rechargeable battery.

The modules included in the leadless pacemaker device 202 represent functionality that may be included in each of the leadless pacemaker devices 202, and may include any discrete and/or integrated electronic circuit components that implement analog and/or digital circuits capable of producing the functions attributed to the modules herein. For example, the modules may include analog circuits, e.g., amplification circuits, filtering circuits, and/or other signal conditioning circuits. The modules may also include digital circuits, e.g., combinational or sequential logic circuits, memory devices, etc. Memory may include any volatile, non-volatile, magnetic, or electrical media, such as a random access memory (RAM), read-only memory (ROM), non-volatile RAM (NVRAM), electrically-erasable programmable ROM (EEPROM), Flash memory, or any other memory device. Furthermore, memory may include instructions that, when executed by one or more processing circuits, cause the modules to perform various functions attributed to the modules herein.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components or integrated within common or separate hardware or software components.

The processing module 230 may communicate with the memory 232. The memory 232 may include computer-readable instructions that, when executed by the processing module 230, cause the processing module 230 to perform the various functions attributed to the processing module 230 herein. The memory 232 may include any volatile, non-volatile, magnetic, or electrical media, such as RAM, ROM, NVRAM, EEPROM, Flash memory, or any other digital media. For example, the memory 232 may include pacing instructions and values, such as the baseline atrial pacing rate, the baseline atrial pacing interval and the baseline AV interval. The pacing instructions and values may be updated by the programmer 212 (FIG. 4). Pacing instructions included in the memory 232 may cause the leadless pacemaker device 202 to operate as described herein.

The processing module 230 may communicate with the signal generator module 234 and the electrical sensing module 236. The signal generator module 234 and the electrical sensing module 236 are electrically coupled to the electrodes 224, 226. The electrical sensing module 236 is configured to monitor signals from the electrodes 224, 226 in order to monitor electrical activity of the heart 206. The signal generator module 234 is configured to deliver electrical stimulation to one or both of the atrium 204 of the heart 206 and the ventricle 210 of the heart 206 via the electrodes 224, 226.

The processing module 230 may control the signal generator module 234 to generate and deliver electrical stimulation to one or both of the atrium 204 of the heart 206 and the ventricle 210 of the heart 206 via the electrodes 224, 226. Electrical stimulation may include pacing pulses. In some examples, electrical stimulation may also include anti-tachycardia pacing (ATP) therapy. The processing module 230 may control the signal generator module 234 to deliver electrical stimulation therapy according to one or more atrial or ventricular therapy programs including pacing instructions and values, which may be stored in the memory 232.

The electrical sensing module 236 may include circuits that acquire electrical signals. Electrical signals acquired by the electrical sensing module 236 may include intrinsic cardiac electrical activity, such as intrinsic atrial and/or intrinsic ventricular cardiac electrical activity. The electrical sensing module 236 may filter, amplify, and digitize the acquired electrical signals to generate raw digital data. The processing module 230 may receive the digitized data generated by the electrical sensing module 236. In some examples, the processing module 230 may perform various digital signal processing operations on the raw data, such as digital filtering.

The processing module 230 may sense cardiac events based on the data received from the electrical sensing module 236. For example, the processing module 230 may sense atrial events based on the data received from the electrical sensing module 236. In some examples, the processing module 230 may sense ventricular activation based on the data received from the electrical sensing module 236. For example, the processing module 230 may detect FFRWs indicative of ventricular activation based on the data received from the electrical sensing module 236.

The sensor 240 may comprise at least one of a variety of different sensors. For example, the sensor 240 may comprise at least one of a pressure sensor, a heart sounds sensor, and an accelerometer. The sensor 240 may generate signals that indicate at least one of an activity level of the patient 208, a hemodynamic pressure, and heart sounds. The processing module 230 may detect, for example, an activity level of the patient 208 based on a sensed accelerometer signal, a hemodynamic pressure signal, and a heart sounds signal based on the signals generated by the sensor 240.

The communication module 238 may include any suitable hardware (e.g., an antenna), firmware, software, or any combination thereof for communicating with another device, such as the programmer 212 or a patient monitor. Under the control of the processing module 230, the communication module 238 may receive downlink telemetry from and send uplink telemetry to other devices, such as the programmer 212 (FIG. 4) or a patient monitor, with the aid of an antenna included in the communication module 238. As described herein, a leadless pacing system may coordinate pacing of the heart 206 based on sensed cardiac electrical and/or mechanical activity without establishment of a communication link between the leadless pacemaker devices 202. Accordingly, the communication module 238 is not required to include functionality that provides for communication between the leadless pacemaker devices 202.

The programmer 212 may be a handheld computing device, desktop computing device, a networked computing device, etc. The programmer 212 may include a computer-readable storage medium having instructions that cause a processor of the programmer 212 to provide the functions attributed to the programmer 212 in the present disclosure. One or both of the leadless pacemaker devices 202 may wirelessly communicate with the programmer 212. For example, the leadless pacemaker devices 202 may transfer data to the programmer 212 and may receive data from the programmer 212. The programmer 212 may also wirelessly program and/or wirelessly charge the leadless pacemaker devices 202.

Data retrieved from the leadless pacemaker devices 202 using the programmer 212 may include cardiac EGMs stored by the leadless pacemaker devices 202 that indicate electrical activity of the heart 206 and marker channel data that indicates the occurrence and timing of sensing, diagnosis, and therapy events associated with the leadless pacemaker devices 202. Data transferred to the leadless pacemaker devices 202 using the programmer 212 may include, for example, operational programs and/or settings for the leadless pacemaker devices 202 that cause the leadless pacemaker devices 202 to operate as described herein.

The processing module 230 may control atrial pacing timing based on the detection of ventricular activation events in a variety of different ways. The manner in which the processing module 230 controls atrial pacing timing may depend on when a ventricular activation event occurs relative to the atrial event that preceded the ventricular activation event. In other words, the manner in which the processing module 230 controls atrial pacing timing may depend on when processing module detects a FFRW or an S1 heart sound relative to the atrial event that preceded the detected FFRW or the detected S1 heart sound.

Figure 7:
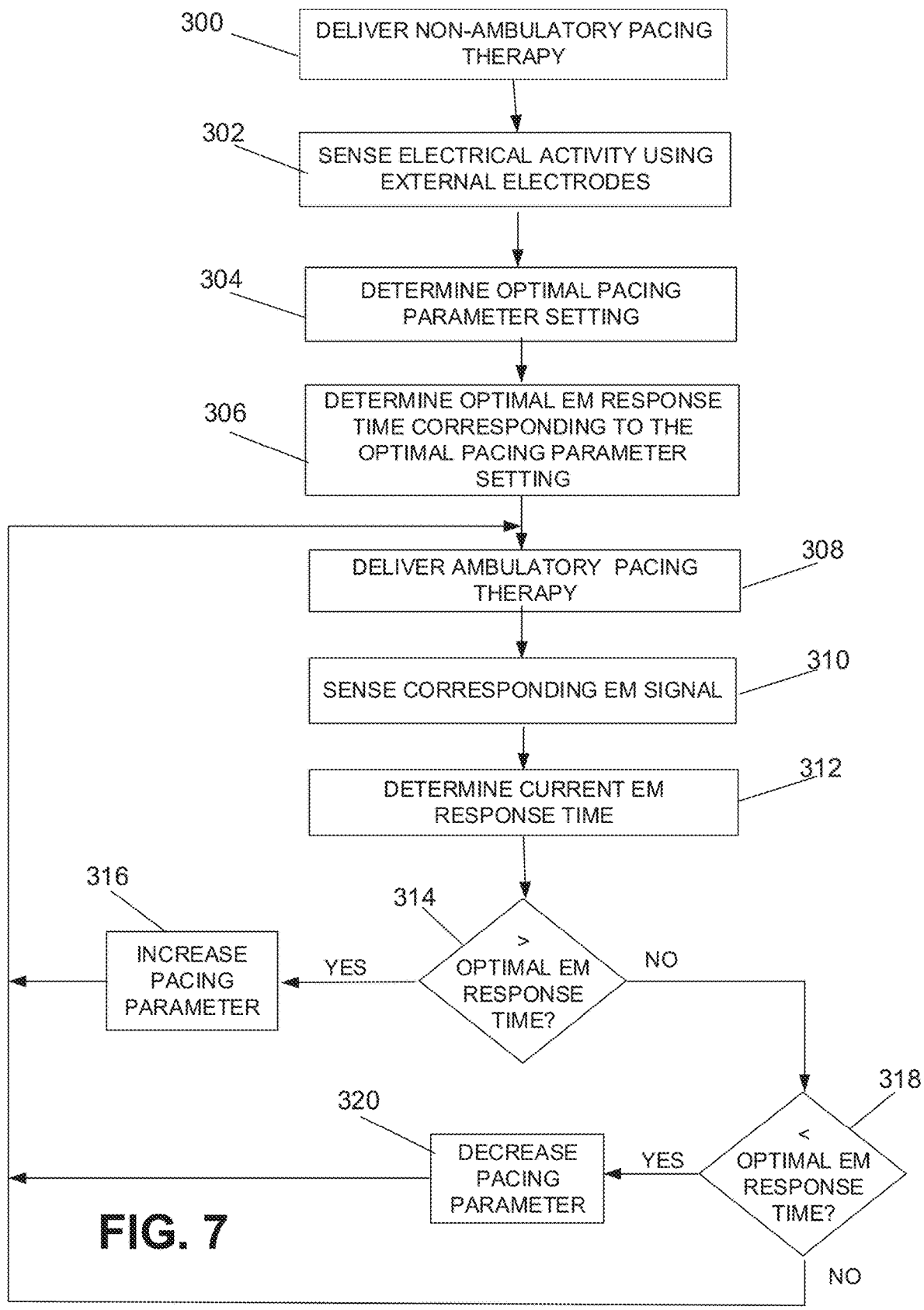
FIG. 7 is a flowchart of a method of delivering a cardiac pacing therapy, according to an example of the present disclosure.

FIG. 7 is a flowchart of a method of delivering a cardiac pacing therapy, according to an example of the present disclosure. As illustrated in FIG. 7, according to one example, a method for delivery of a pacing therapy includes delivering a non-ambulatory pacing therapy, Block 300, i.e., pacing therapy delivered while the electrode apparatus 110 is worn by the patient, via a pacing device implanted within the patient. Electrical activation information associated with one or more regions of a patient's heart is sensed, Block 302, using the external electrodes 112 of the electrode apparatus 110 described above, for example. The computing apparatus 140 receives the sensed electrical activation information and determines an optimal pacing parameter setting for one or more pacing parameters, or combination of pacing parameters, associated with the pacing therapy delivered by the pacing device based on the received sensed electrical activation information, Block 304. Once the optimal pacing parameter setting is determined, an optimal electromechanical (EM) response time corresponding to the optimal pacing parameter setting is determined, Block 306.

During the determination of the optimal EM response time, Blocks 300-306, the computing apparatus 140 receives the electrical activity sensed by the ECG belt electrodes 112 positioned on the patient, and generates, based on the sensed electrical activity, electrical heterogeneity information resulting for different values or settings of a pacing therapy parameter during non-ambulatory pacing. The electrical activity monitored using the ECG belt described above can be used to evaluate any one parameter or combination of pacing parameters including, but not limited to pacing parameters such as an AV delay, which controls the timing of ventricular pacing pulses relative to an atrial depolarization. Other examples of pacing parameters may include ventricular-to-ventricular (V-V) delay, which basically measures the interval before and after left ventricular pacing is delivered relative to right ventricular pacing, pacing rate, pacing output, pacing pulse width, etc. Body-surface isochronal maps of ventricular activation can be constructed using the electrical activity sensed during the delivery of non-ambulatory pacing therapy by the pacing device. The sensed electrical activity and/or the map of ventricular activation can be used to generate the electrical heterogeneity information, including determining metrics of electrical heterogeneity.

The metrics of electrical heterogeneity can include a metric of standard deviation of activation times (SDAT) of electrodes on a torso of the patient and/or a metric of mean left ventricular activation time (LVAT) of electrodes on the left side of the torso of the patient. A metric of LVAT may be determined from electrodes on both the anterior and posterior surfaces. The metrics of electrical heterogeneity information can include a metric of mean right ventricular activation time (RVAT) of electrodes on the right side of the torso of the patient. A metric of RVAT may be determined from electrodes on both the anterior and posterior surfaces. The metrics of electrical heterogeneity can include a metric of mean total activation time (mTAT) taken from a plurality of electrode signals from both sides of the torso of the patient, or it may include other metrics (e.g., standard deviation, interquartile deviations, a difference between a latest activation time and earliest activation time) reflecting a range or dispersion of activation times on a plurality of electrodes located on the right side of the patient torso or left side of the patient torso, or combining both right and left sides of the patient torso.

In at least one embodiment, the determination of the optimal electrical activation may based on at least one metric of electrical heterogeneity generated from electrical activity of during non-ambulatory pacing. For example, the at least one metric can include at least one of a standard deviation of activation times (SDAT) and a left ventricular activation time (LVAT). As an example, the optimal electrical activation may be determined using a pair of isochronal maps from the anterior aspect of the torso and corresponding maps from the posterior aspect of the torso.

In one example, an early activation portion of the anterior aspect is compared to an early activation portion of the posterior aspect and for each of multiple settings of a pacing parameter and the optimal pacing parameter is determined based on the results of the comparisons. For example, the computing device may generate an isochronal map of SDAT and LVAT, or a combination of the two during intrinsic synchronized conduction. Next the computing device 140 generates the same isochronal map (SDAT, LVAT or both) during pacing using a first parameter setting and stores the resulting map or maps. The parameter setting is then adjusted to a second parameter setting and the computing device 140 delivers the pacing therapy using the second parameter setting, generates the same isochronal map or maps (SDAT, LVAT or both) during pacing using he second parameter setting, and stores the resulting map or maps.

This process is repeated for a predetermined number of parameter settings, and once the isochronal maps have been determined for all of the different predetermined parameter settings, the computing device determines which of the resulting stored isochronal maps results in the largest improvement (reduction) in electrical heterogeneity during pacing compared to the determined intrinsic synchronized conduction with respect to SDAT, LVAT or a combination of SDAT/LVAT. In one example, if there are two maps that are both determined to result in the largest improvement in electrical heterogeneity, the computing device 140 determines which of LVAT associated with the two maps results in the largest improvement compared to the LVAT that was determined during intrinsic synchronized conduction, and identifies the associated parameter setting as the optimal pacing parameter setting, Block 320.

Returning to FIG. 7, during subsequent delivery of ambulatory pacing, Block 308, i.e., pacing therapy that is delivered once the electrode apparatus 110 is no longer worn by the patient, the pacing device senses a corresponding EM signal, Block 310, and determines, in response to the sensed EM signal, a current EM response time, Block 312. The pacing device then determines whether the current EM response time is greater than the determined optimal EM response time, Block 314. In one example, the current EM response time is determined to be greater than the optimal response time in Block 314 if the current EM response time is greater than the sum of the optimal response time and a predetermined range tolerance. For example, the range tolerance may be set as a percentage (for e.g. 5%, 10%, 15%) of the optimal response time. In another example, the range tolerance may be specified by a timing threshold (e.g. 10 ms, 15 ms, 20 ms, 25 ms), so that the current EM response time is determined to be greater than the determined optimal EM response time if the current EM response time is greater than the sum of the optimal EM response time and the range tolerance.

In an example in which the pacing parameter setting corresponds to AV-delay, if the current EM response time is greater than the determined optimal EM response time, Yes in Block 314, the AV delay is too short and therefore the pacing parameter is increased, Block 316, and the pacing device delivers the pacing therapy using the increased pacing parameter, Block 308. If the current EM response time is determined not to be greater than the determined optimal EM response time, No in Block 314, the pacing device determines whether the current EM response time is less than the determined optimal EM response time, Block 318. In one example, the current EM response time is determined to be less than the optimal response time in Block 318 if the current EM response time is less than the optimal response time minus the predetermined range tolerance.

If the current EM response time is determined to be less than the determined optimal EM response time, Yes in Block 318, the device may be pacing at longer AV delays than optimal and therefore the pacing parameter is decreased, Block 320 and the pacing device delivers the pacing therapy using the decreased pacing parameter, Block 308. On the other hand, if the current EM response time is determined not to be greater than the optimal EM response time, No in Block 314, and not to be less than the optimal EM response time, No in Block 318, the pacing device makes no adjustment of the pacing parameter and continues to use the same pacing parameter setting. In this way, by adjusting the pacing parameter setting in response to changes in the sensed EM signal, the delivery of a pacing therapy according to the present disclosure maintains the optimal EM response time during ambulatory pacing.

Figure 8:
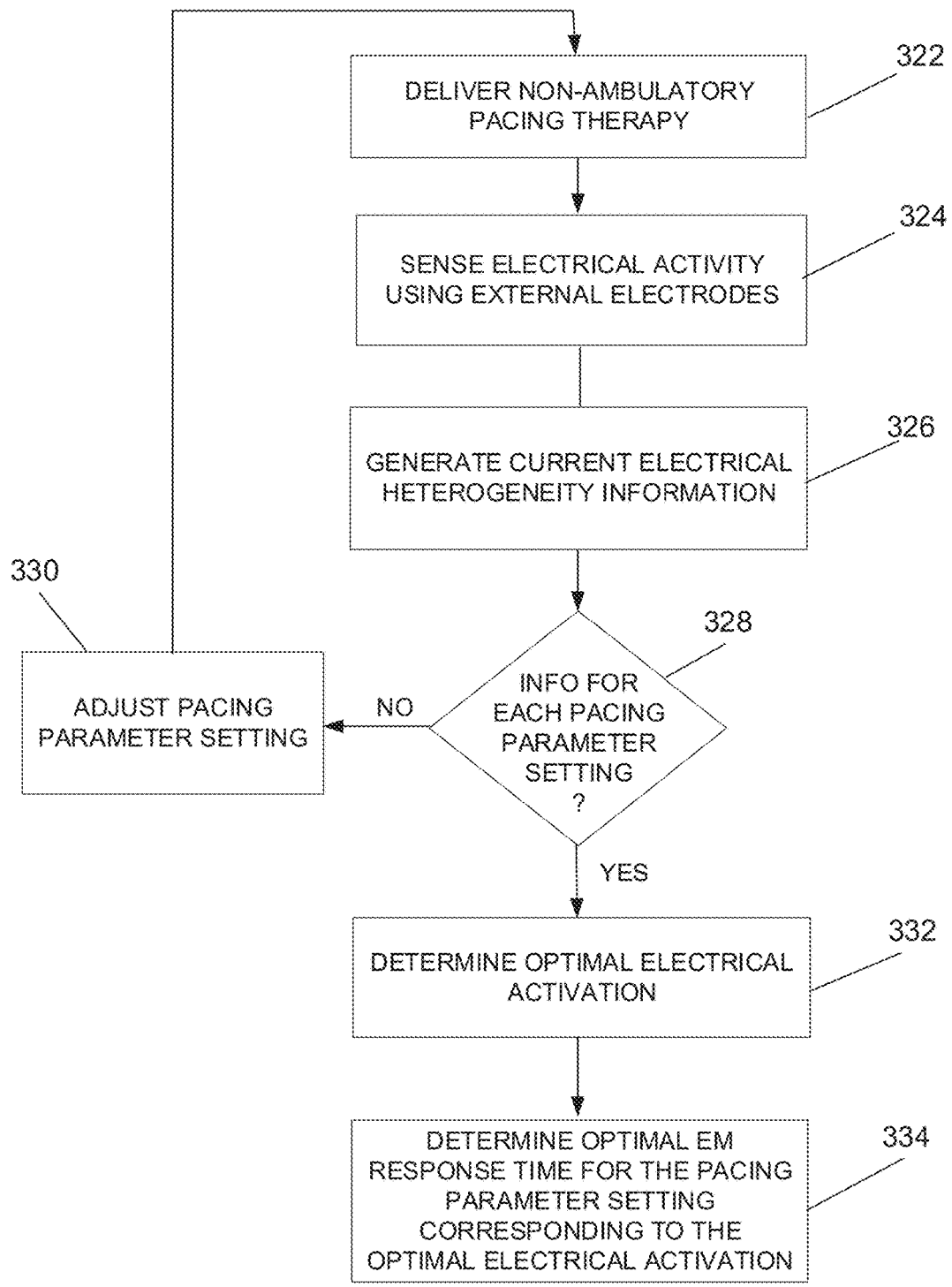
FIG. 8 is a flowchart of a method of determining an optimal EM response time for one or more pacing parameters associated with delivery of a pacing therapy, according to an example of the present disclosure.

FIG. 8 is a flowchart of a method of determining an optimal EM response time for one or more pacing parameters associated with delivery of a pacing therapy, according to an example of the present disclosure. In one example, during non-ambulatory pacing, the computing apparatus 140 may determine, based on the received sensed electrical activation information, a patient specific optimal EM response time associated with one or more pacing parameters that results in synchronized pacing therapy for the patient. For example, according to the present disclosure, in order to determine the optimal EM response time, the pacing therapy system determines heterogeneity information for each of a multiple number of one or more pacing parameter settings and determines the pacing parameter setting of the multiple pacing parameters settings that results in the optimal electrical activation, i.e., synchronized conduction, based on the heterogeneity information for each setting.

For example, as illustrated in FIG. 8, during delivery of non-ambulatory pacing therapy, pacing therapy is delivered to the patient using an initial setting for the pacing parameter, Block 322, electrical activity associated with one or more regions of a patient's heart is sensed, Block 324, using external electrodes 112 of the electrode apparatus 110 described above, for example. The computing apparatus 140 receives the sensed electrical activation information and generates current electrical heterogeneity information associated with the current pacing parameter setting, Block 326. Once heterogeneity information is generated for the current parameter setting, Block 326, the computing apparatus 140 determines whether heterogeneity information has been generated for a predetermined number of different parameter settings, Block 328. In one example, heterogeneity information may be for generated AV delays equal to 40%, 50%, 60%, 70% and 80% of patient's intrinsic AV delay. In another example, the heterogeneity information may be derived for multiple AV settings starting with a short AV delay of 60 ms and increasing the AV delay in steps of 10 or 20 ms, till the patient's intrinsic AV interval, Block 328.

If it is determined that heterogeneity information has not been generated for each of the predetermined number of different parameter settings, No in Block 328, the current pacing parameter setting is adjusted to the next parameter setting, Block 330, the pacing device delivers the pacing therapy using the adjusted pacing parameter, Block 322, and electrical heterogeneity information is generated for the adjusted pacing parameter setting, Blocks 324 and 326. Once heterogeneity information has been generated for each of the predetermined number of different parameter settings, Yes in Block 328, an optimal electrical activation or synchronization pattern is determined from the electrical heterogeneity information, Block 332, described below, and an optimal EM response time for the pacing parameter corresponding to the optimal electrical activation is determined, Block 324, described below.

Figure 9:
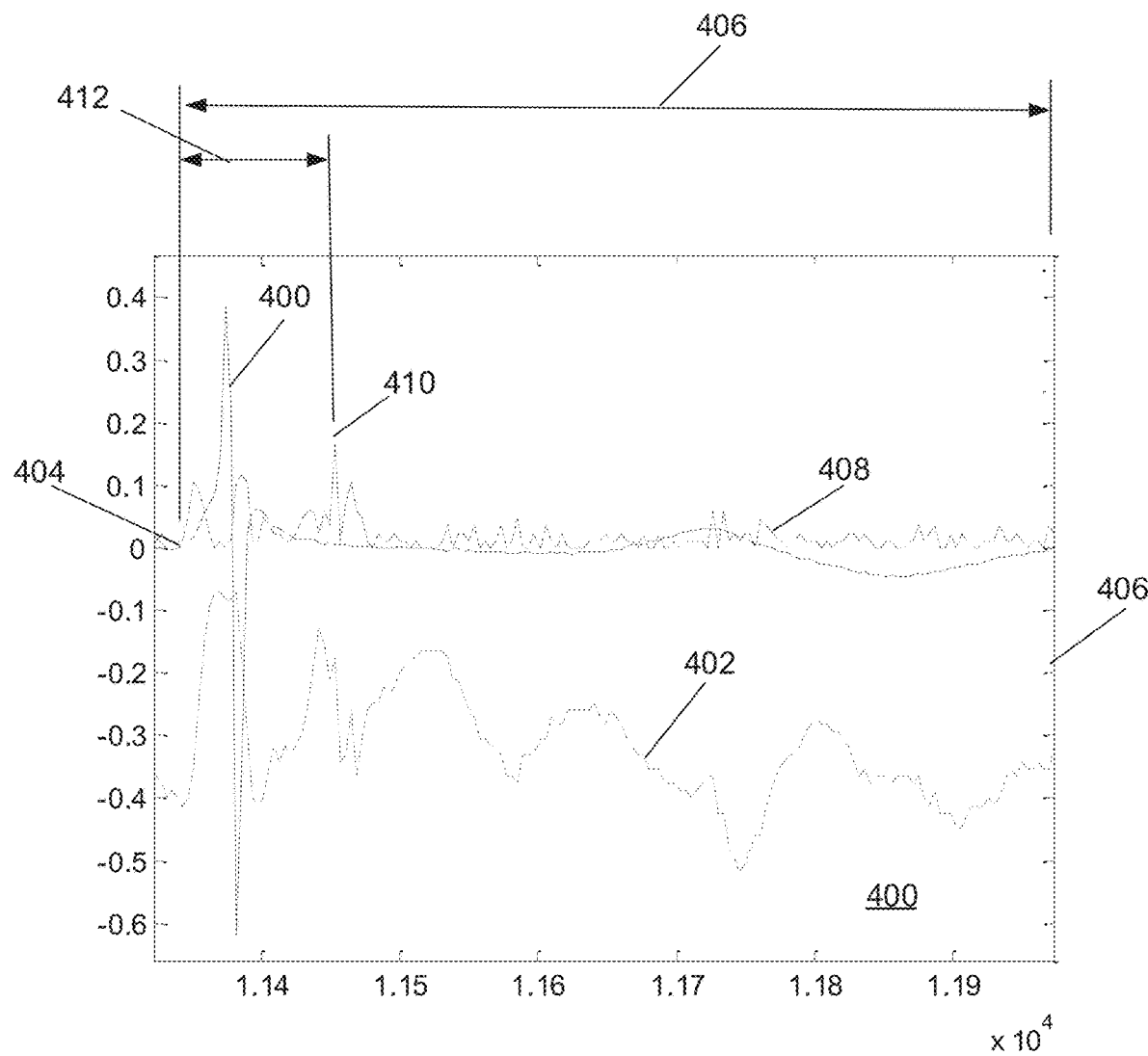
FIG. 9 is a graphical representation of determining an optimal EM response time for delivery of a pacing therapy according to an example of the present disclosure.

FIG. 9 is a graphical representation of determining of an optimal EM response time for delivery of a pacing therapy according to an example of the present disclosure. As illustrated in FIG. 9, once the optimal electrical activation is determined in Block 332 of FIG. 8, in order to determine the optimal EM response time for the pacing parameter setting corresponding to the optimal electrical activation, Block 334 of FIG. 8, the computing apparatus 140 determines a near-field signal 400 sensed by sensing electrodes of the pacing device, and an EM signal 402 sensed by an EM sensor of the pacing device. The computing apparatus 140 identifies timing of the occurrence of a ventricular pace (VP) event 404 from the near-field signal 400 and determines a time window extending a predetermined time period 406 from the sensed VP event 404. The computing device 140 determines a rectified derivative signal 408 of the EM signal 402 and determines a maximum 410 of the rectified derivative signal 408 that occurs within the time window 406. As a result, an optimal EM response time is determined as being a time period 412 extending between the VP signal 404 and the maximum 410 of the rectified derivative signal 408. The pacing parameter setting corresponding to the optimal electrical activation and the corresponding determined optimal EM response time 412 are stored within the pacing device.

Figure 10:
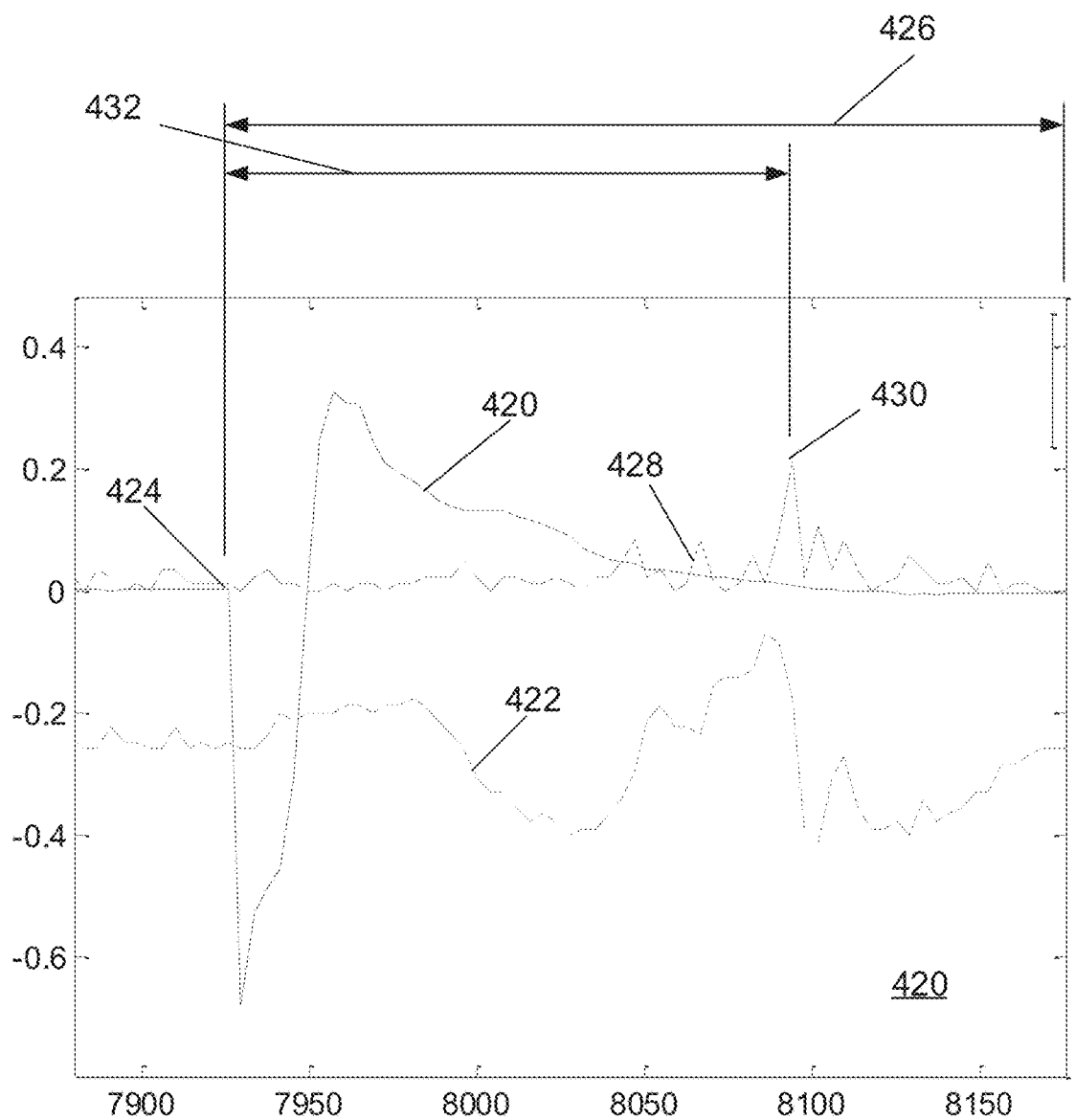
FIG. 10 is graphical representation of an electro-mechanical (EM) signal sensed during delivery of an ambulatory pacing therapy, according to an example of the present disclosure.

FIG. 10 is graphical representation of an electro-mechanical (EM) signal sensed during delivery of an ambulatory pacing therapy, according to an example of the present disclosure. Once the optimal EM response time 414 has been determined by the computing apparatus 140 during delivery of non-ambulatory pacing therapy, Block 334 of FIG. 8, and the patient becomes ambulatory, the pacing device delivers ambulatory pacing therapy using the determined optimal pacing parameter setting corresponding to the optimal electrical activation. As illustrated in FIG. 10, during delivery of the ambulatory pacing therapy, the pacing device determines a near-field signal 420 sensed by sensing electrodes of the pacing device, and an EM signal 422 sensed by an EM sensor of the pacing device. The pacing device identifies timing of the occurrence of a ventricular pace (VP) event 424 from the near-field signal 420 and determines a time window extending a predetermined time period 426 from the sensed VP event 424. The pacing device determines a rectified derivative signal 428 of the EM signal 422 and determines a maximum 430 of the rectified derivative signal 428 that occurs within the time window 426. As a result, a current EM response time is determined as being a time period 432 extending between the sensing of the VP event 424 and the maximum 430 of the rectified derivative signal 428.

In one example, an implantable medical device system may include the ECG belt 110 and computing device 140, and one or more leadless pacing device 202 described above, and the pacing parameter may be an AV-delay. In such an example, electrical activity of tissue of a patient is sensed from external electrodes 110 during delivery of non-ambulatory pacing therapy by the leadless pacing device 202 and an optimal EM response time is determined in response to the sensed electrical activity. During subsequent delivering of ambulatory pacing therapy from the leadless pacing device 202, an EM signal is sensed by an EM sensor 240 of the leadless pacing device 202. A current EM response time is determined in response to the sensed EM signal, and a pacing parameter setting of the ambulatory pacing therapy may be adjusted if the current EM response time is determined to be either greater than the optimal EM response time or less than the optimal EM response time.

The exemplary systems, methods, and graphical user interfaces described herein is shown as being utilized with respect to the implantation and configuration of a leadless pacing device, it is understood that the exemplary systems, methods, and graphical user interfaces described herein may also utilized in an implantable medical device (IMD) having an electro-mechanical sensor and/or one or more leads configured to be located proximate one or more portions of a patient's heart.

ILLUSTRATIVE EMBODIMENTS

Embodiment 1

A method of delivering a cardiac pacing therapy, comprising:
  delivering a non-ambulatory pacing therapy from a pacing device;
  sensing electrical activity of tissue of a patient from a plurality of external electrodes during the delivered non-ambulatory pacing therapy;
  determining an optimal electro-mechanical (EM) response time in response to the sensed electrical activity;
  delivering an ambulatory pacing therapy from the pacing device;
  sensing an EM signal from an EM sensor of the pacing device;
  determining a current EM response time in response to the sensed EM signal;
  comparing the current EM response time to the optimal EM response time; and
  adjusting a pacing parameter setting of the ambulatory pacing therapy in response to the comparing.

Embodiment 2

The embodiment of claim 1, further comprising delivering the non-ambulatory pacing using a plurality of different values for the pacing parameter setting, wherein determining the optimal EM response time comprises:
  determining electrical heterogeneity information for each value of the plurality of different values;
  determining an optimal electrical activation in response to the determined electrical heterogeneity information; and
  determining the optimal EM response time in response to the determined optimal electrical activation.

Embodiment 3

The embodiment of any of embodiments 1 and 2, wherein determining the optimal electrical activation in response to the determined electrical heterogeneity information comprises:
  determining an isochronal map during intrinsic synchronized conduction;
  determining isochronal maps for value of each of the plurality of different values for the pacing parameter setting; and
  determining an optimal value of the plurality of different values that results in the greatest reduction in electrical heterogeneity during pacing compared to the determined intrinsic synchronized conduction.

Embodiment 4

The method of any of claims 1-3, further comprising storing the value of the plurality of different values for the pacing parameter corresponding to the optimal electrical activation and the determined EM response time within a memory of the pacing device.

Embodiment 5

The method of embodiments 1-4, further comprising:
  sensing a near-field signal during delivery of the non-ambulatory pacing therapy via sensing electrodes of the pacing device;
  sensing delivery of a ventricular pace (VP) event from the sensed near-field signal;
  determining a maximum of a rectified derivative of the EM signal within a time window extending a predetermined time period from the sensed VP event; and
  determining the optimal EM response time as a time period extending between the VP event and the maximum of the rectified derivative signal.

Embodiment 6

The method of any of embodiments 1-5, further comprising:
  sensing a near-field signal during delivery of the ambulatory pacing therapy via sensing electrodes of the pacing device;
  sensing delivery of a ventricular pace (VP) event from the sensed near-field signal;
  determining a maximum of a rectified derivative of the EM signal within a time window extending a predetermined time period from the sensed VP event; and
  determining the current EM response time as a time period extending between the VP event and the maximum of the rectified derivative signal.

Embodiment 7

The method of any of embodiments 1-4, further comprising:
  sensing a first near-field signal during delivery of the non-ambulatory pacing therapy via sensing electrodes of the pacing device;
  sensing a first ventricular pace (VP) event from the sensed first near-field signal;
  determining a first maximum of a rectified derivative of the EM signal within a time window extending a predetermined time period from the sensed first VP event;
  determining the optimal EM response time as a time period extending between the first VP event and the first maximum of the rectified derivative signal;

sensing a second near-field signal during delivery of the ambulatory pacing therapy via the sensing electrodes of the pacing device;

sensing a second ventricular pace (VP) event from the sensed second near-field signal during delivery of the ambulatory pacing;

determining a second maximum of a rectified derivative of the EM signal within a time window extending a predetermined time period from the second sensed VP event; and determining the current EM response time as a time period extending between the second VP event and the second maximum of the rectified derivative signal.

Embodiment 8

The method of embodiment 7, further comprising:

increasing the pacing parameter setting in response to the current EM response time being greater than the optimal EM response time; and decreasing the pacing parameter setting in response to the current EM response time being less than the optimal EM response time.

Embodiment 9

The method of embodiments 1-8, wherein the pacing device comprises a leadless pacing device, the EM signal comprises an accelerometer signal, and the pacing parameter setting comprises timing of an atrioventricular delay.

Embodiment 10

An implantable medical device system for delivering a pacing therapy, comprising:

a pacing device comprising:
  one or more electrodes for sensing cardiac signals and delivering the pacing therapy, the pacing therapy comprising one of a non-ambulatory pacing therapy and an ambulatory pacing therapy;
  a processor configured to configured to control delivery of the pacing therapy via the one or more electrodes; and
  an electromechanical (EM) sensor to sense an EM signal of the patient in response to the delivered pacing therapy;

a plurality of external electrodes capable of being positioned along a torso of a patient to sense electrical activity of tissue of the patient; and a computing apparatus electrically coupled to the plurality of external electrodes, wherein the computing apparatus is configured to determine an optimal electromechanical (EM) response time in response to the sensed electrical activity from the plurality of external electrodes during delivery of non-ambulatory pacing therapy by the pacing device, and wherein the processor of the pacing device is further configured to sense an EM signal from the EM sensor during delivery of ambulatory pacing, determine a current EM response time in response to the sensed EM signal, compare the current EM response time determined by the processor of the pacing device during delivery of ambulatory pacing to the optimal EM response time determined by the computing apparatus during delivery of non-ambulatory pacing therapy by the pacing device, and adjust a pacing parameter setting for delivering the ambulatory pacing therapy in response to the comparing.

Embodiment 11

The system of embodiment 10, wherein the processor of the pacing device is configured to deliver the non-ambulatory pacing using a plurality of different values for the pacing parameter setting, and wherein the computing apparatus is configured to determine electrical heterogeneity information for each value of the plurality of different values, determine an optimal electrical activation in response to the determined electrical heterogeneity information, and determine the optimal EM response time in response to the determined optimal electrical activation.

Embodiment 12

The system of any of embodiments 10 and 11, wherein the processor of the pacing device is configured to determine an isochronal map during intrinsic synchronized conduction, determine isochronal maps for value of each of the plurality of different values for the pacing parameter setting, and determine an optimal value of the plurality of different values that results in the greatest reduction in electrical heterogeneity during pacing compared to the determined intrinsic synchronized conduction.

Embodiment 13

The system of any of embodiments claim 10-12, the pacing device further comprising a memory configured to store the value of the plurality of different values for the pacing parameter corresponding to the optimal electrical activation and the determined EM response time.

Embodiment 14

The system of any of embodiments 10-13, wherein the processor of the pacing device is configured to sense a near-field signal during delivery of the non-ambulatory pacing therapy via sensing electrodes of the pacing device, and sense delivery of a ventricular pace (VP) event from the sensed near-field signal, and wherein the computing apparatus is configured to determine a maximum of a rectified derivative of the EM signal within a time window extending a predetermined time period from the sensed VP event, and determine the optimal EM response time as a time period extending between the VP event and the maximum of the rectified derivative signal.

Embodiment 15

The system of any of embodiments 10-14, wherein the processor of the pacing device is configured to sense a near-field signal during delivery of the ambulatory pacing therapy via the one or more electrodes, sense delivery of a ventricular pace (VP) event from the sensed near-field signal, determine a maximum of a rectified derivative of the EM signal within a time window extending a predetermined time period from the sensed VP event, and determine the current EM response time as a time period extending between the VP event and the maximum of the rectified derivative signal.

Embodiment 16

The system of any of embodiments 10-13, wherein the processor of the pacing device is configured to sense a first near-field signal during delivery of the non-ambulatory pacing therapy via sensing electrodes of the pacing device, and sense a first ventricular pace (VP) event from the sensed near-field signal, and wherein the computing apparatus is configured to determine a first maximum of a rectified derivative of the EM signal within a time window extending a predetermined time period from the first sensed VP event, and determine the optimal EM response time as a time period extending between the first VP event and the first maximum of the rectified derivative signal, and wherein the processor of the pacing device is configured to sense a second near-field signal during delivery of the ambulatory pacing therapy via the one or more electrodes, sense a second ventricular pace (VP) event from the second sensed near-field signal, determine a second maximum of a rectified derivative of the EM signal within a time window extending a predetermined time period from the second sensed VP event, and determine the current EM response time as a time period extending between the second VP event and the second maximum of the rectified derivative signal.

Embodiment 17

The system of any of embodiments 10-16, wherein the processor of the pacing device is configured to increase the pacing parameter setting in response to the current EM response time being greater than the optimal EM response time and decrease the pacing parameter setting in response to the current EM response time being less than the optimal EM response time.

Embodiment 18

The system of any of embodiments 10-17, wherein the pacing device comprises a leadless pacing device, the EM signal comprises an accelerometer signal, and the pacing parameter setting comprises an atrioventricular delay.

Embodiment 19

An implantable medical device for delivering a pacing therapy comprising:
 means for delivering a non-ambulatory pacing therapy from a pacing device;
 means for sensing electrical activity of tissue of a patient from a plurality of external electrodes during the delivered non-ambulatory pacing therapy;
 means for determining an optimal electro-mechanical (EM) response time in response to the sensed electrical activity;
 means for delivering an ambulatory pacing therapy from the pacing device;
 means for sensing an EM signal from an EM sensor of the pacing device;
 means for determining a current EM response time in response to the sensed EM signal;
 means for comparing the current EM response time to the optimal EM response time; and
 means for adjusting a pacing parameter setting of the ambulatory pacing therapy in response to the comparing.

Embodiment 20

The device of embodiment 19, wherein the pacing device comprises a leadless pacing device, the EM signal comprises an accelerometer signal, and the pacing parameter setting comprises timing of an atrioventricular delay.

Embodiment 21

A non-transitory computer readable medium storing instructions which cause a cardiac pacing device to perform a method comprising:
 delivering a non-ambulatory pacing therapy from a pacing device;
 sensing electrical activity of tissue of a patient from a plurality of external electrodes during the delivered non-ambulatory pacing therapy;
 determining an optimal electro-mechanical (EM) response time in response to the sensed electrical activity;
 delivering an ambulatory pacing therapy from the pacing device;
 sensing an EM signal from an EM sensor of the pacing device;
 determining a current EM response time in response to the sensed EM signal;
 comparing the current EM response time to the optimal EM response time; and
 adjusting a pacing parameter setting of the ambulatory pacing therapy in response to the comparing.

What is claimed:
1. A method of delivering a cardiac pacing therapy, comprising:
 delivering a non-ambulatory pacing therapy from a pacing device;
 sensing electrical activity of tissue of a patient from a plurality of external electrodes during the delivered non-ambulatory pacing therapy;
 sensing a non-ambulatory electro-mechanical (EM) signal from an EM sensor of the pacing device;
 determining a time period between a non-ambulatory ventricular pace (VP) event and a mechanical response based on the non-ambulatory EM signal;
 determining an optimal EM response time based the determined time period;
 delivering an ambulatory pacing therapy from the pacing device;
 sensing an ambulatory EM signal from the EM sensor of the pacing device;
 determining a current EM response time in response to the sensed ambulatory EM signal;
 comparing the current EM response time to the optimal EM response time; and
 adjusting a pacing parameter setting of the ambulatory pacing therapy in response to the comparing.

2. The method of claim 1, further comprising delivering the non-ambulatory pacing using a plurality of different values for the pacing parameter setting, wherein determining the optimal EM response time comprises:
 determining electrical heterogeneity information for each value of the plurality of different values based on the sensed electrical activity from the plurality of external electrodes;
 determining an optimal electrical activation in response to the determined electrical heterogeneity information; and
 determining the optimal EM response time in response to the determined optimal electrical activation.

3. The method of claim 2, wherein determining the optimal electrical activation in response to the determined electrical heterogeneity information comprises:

determining an isochronal map during intrinsic synchronized conduction;
determining isochronal maps for value of each of the plurality of different values for the pacing parameter setting; and
determining an optimal value of the plurality of different values that results in the greatest reduction in electrical heterogeneity during pacing compared to the determined intrinsic synchronized conduction.

4. The method of claim 2, further comprising storing the value of the plurality of different values for the pacing parameter corresponding to the optimal electrical activation and the determined EM response time within a memory of the pacing device.

5. The method of claim 1, further comprising:
sensing a near-field signal during delivery of the non-ambulatory pacing therapy via sensing electrodes of the pacing device;
sensing delivery of the non-ambulatory VP event from the sensed near-field signal;
determining a maximum of a rectified derivative of the non-ambulatory EM signal within a time window extending a predetermined time period from the sensed non-ambulatory VP event; and
determining the optimal EM response time as a time period extending between the non-ambulatory VP event and the maximum of the rectified derivative signal.

6. The method of claim 1, further comprising:
sensing a near-field signal during delivery of the ambulatory pacing therapy via sensing electrodes of the pacing device;
sensing delivery of an ambulatory VP event from the sensed near-field signal;
determining a maximum of a rectified derivative of the ambulatory EM signal within a time window extending a predetermined time period from the sensed ambulatory VP event; and
determining the current EM response time as a time period extending between the ambulatory VP event and the maximum of the rectified derivative signal.

7. The method of claim 1, further comprising:
sensing a first near-field signal during delivery of the non-ambulatory pacing therapy via sensing electrodes of the pacing device;
sensing a non-ambulatory VP event from the sensed first near-field signal;
determining a maximum of a rectified derivative of the non-ambulatory EM signal within a time window extending a predetermined time period from the sensed non-ambulatory VP event;
determining the optimal EM response time as a time period extending between the non-ambulatory VP event and the maximum of the rectified derivative of the non-ambulatory EM signal;
sensing a second near-field signal during delivery of the ambulatory pacing therapy via the sensing electrodes of the pacing device;
sensing an ambulatory VP event from the sensed second near-field signal during delivery of the ambulatory pacing;
determining a maximum of a rectified derivative of the ambulatory EM signal within a time window extending a predetermined time period from the sensed ambulatory VP event; and determining the current EM response time as a time period extending between the ambulatory VP event and the maximum of the rectified derivative of the ambulatory EM signal.

8. The method of claim 7, further comprising:
increasing the pacing parameter setting in response to the current EM response time being greater than the optimal EM response time; and
decreasing the pacing parameter setting in response to the current EM response time being less than the optimal EM response time.

9. The method of claim 1, wherein the pacing device comprises a leadless pacing device, the EM sensor comprises an accelerometer, and the pacing parameter setting comprises timing of an atrioventricular delay.

10. An implantable medical device system for delivering a pacing therapy, comprising:
a pacing device comprising:
one or more electrodes for sensing cardiac signals and delivering the pacing therapy, the pacing therapy comprising one of a non-ambulatory pacing therapy and an ambulatory pacing therapy;
a processor configured to control delivery of the pacing therapy via the one or more electrodes; and
an electromechanical (EM) sensor to sense a non-ambulatory EM signal of the patient in response to the delivered non-ambulatory pacing therapy and an ambulatory EM signal of the patient in response to the delivered ambulatory pacing therapy;
a plurality of external electrodes capable of being positioned along a torso of a patient to sense electrical activity of tissue of the patient; and
a computing apparatus electrically coupled to the plurality of external electrodes, wherein the computing apparatus is configured to:
determine a time period between a non-ambulatory ventricular pace (VP) event and a mechanical response based on the non-ambulatory EM signal; and
determine an optimal EM response time based the determined time period during delivery of non-ambulatory pacing therapy by the pacing device, and wherein the processor of the pacing device is further configured determine a current EM response time in response to the sensed ambulatory EM signal, compare the current EM response time determined by the processor of the pacing device during delivery of ambulatory pacing to the optimal EM response time determined by the computing apparatus during delivery of non-ambulatory pacing therapy by the pacing device, and adjust a pacing parameter setting for delivering the ambulatory pacing therapy in response to the comparing.

11. The system of claim 10, wherein the processor of the pacing device is configured to deliver the non-ambulatory pacing using a plurality of different values for the pacing parameter setting, and wherein the computing apparatus is configured to determine electrical heterogeneity information for each value of the plurality of different values based on the sensed electrical activity from the plurality of external electrodes, determine an optimal electrical activation in response to the determined electrical heterogeneity information, and determine the optimal EM response time in response to the determined optimal electrical activation.

12. The system of claim 11, wherein the processor of the pacing device is configured to determine an isochronal map during intrinsic synchronized conduction, determine isochronal maps for value of each of the plurality of different values for the pacing parameter setting, and determine an optimal value of the plurality of different values that results in the greatest reduction in electrical heterogeneity during pacing compared to the determined intrinsic synchronized conduction.

13. The system of claim 11, the pacing device further comprising a memory configured to store the value of the plurality of different values for the pacing parameter corresponding to the optimal electrical activation and the determined optimal EM response time.

14. The system of claim 10, wherein the processor of the pacing device is configured to sense a near-field signal during delivery of the non-ambulatory pacing therapy via sensing electrodes of the pacing device, and sense delivery of a VP event from the sensed near-field signal, and wherein the computing apparatus is configured to determine a maximum of a rectified derivative of the non-ambulatory EM signal within a time window extending a predetermined time period from the sensed VP event, and determine the optimal EM response time as a time period extending between the VP event and the maximum of the rectified derivative signal.

15. The system of claim 10, wherein the processor of the pacing device is configured to sense a near-field signal during delivery of the ambulatory pacing therapy via the one or more electrodes, sense delivery of a ventricular pace (VP) event from the sensed near-field signal, determine a maximum of a rectified derivative of the ambulatory EM signal within a time window extending a predetermined time period from the sensed VP event, and determine the current EM response time as a time period extending between the VP event and the maximum of the rectified derivative signal.

16. The system of claim 10, wherein the processor of the pacing device is configured to:
sense a first near-field signal during delivery of the non-ambulatory pacing therapy via sensing electrodes of the pacing device; and
sense a non-ambulatory VP event from the sensed near-field signal, and wherein the computing apparatus is configured to:
determine a maximum of a rectified derivative of the non-ambulatory EM signal within a time window extending a predetermined time period from the sensed non-ambulatory VP event; and
determine the optimal EM response time as a time period extending between the non-ambulatory VP event and the maximum of the rectified derivative of the non-ambulatory EM signal, and wherein the processor of the pacing device is configured to sense a second near-field signal during delivery of the ambulatory pacing therapy via the one or more electrodes, sense an ambulatory VP event from the second sensed near-field signal, determine a maximum of a rectified derivative of the ambulatory EM signal within a time window extending a predetermined time period from the ambulatory VP event, and determine the current EM response time as a time period extending between the ambulatory VP event and the maximum of the rectified derivative of the ambulatory EM signal.

17. The system of claim 10, wherein the processor of the pacing device is configured to increase the pacing parameter setting in response to the current EM response time being greater than the optimal EM response time and decrease the pacing parameter setting in response to the current EM response time being less than the optimal EM response time.

18. The system of claim 10, wherein the pacing device comprises a leadless pacing device, the EM sensor comprises an accelerometer, and the pacing parameter setting comprises an atrioventricular delay.

19. An implantable medical device for delivering a pacing therapy comprising:
means for delivering a non-ambulatory pacing therapy from a pacing device;
means for sensing electrical activity of tissue of a patient from a plurality of external electrodes during the delivered non-ambulatory pacing therapy;
means for sensing a non-ambulatory electro-mechanical (EM) signal from an EM sensor of the pacing device;
means for determining a time period between a non-ambulatory ventricular pace (VP) event and a mechanical response based on the non-ambulatory EM signal;
means for determining an optimal EM response time based the determined time period
means for delivering an ambulatory pacing therapy from the pacing device;
means for sensing an ambulatory EM signal from the EM sensor of the pacing device;
means for determining a current EM response time in response to the sensed ambulatory EM signal;
means for comparing the current EM response time to the optimal EM response time; and
means for adjusting a pacing parameter setting of the ambulatory pacing therapy in response to the comparing.

20. The device of claim 19, wherein the pacing device comprises a leadless pacing device, the EM sensor comprises an accelerometer, and the pacing parameter setting comprises timing of an atrioventricular delay.

21. A non-transitory computer readable medium storing instructions which cause a cardiac pacing device to perform a method comprising:
delivering a non-ambulatory pacing therapy from a pacing device;
sensing electrical activity of tissue of a patient from a plurality of external electrodes during the delivered non-ambulatory pacing therapy;
sensing a non-ambulatory electro-mechanical (EM) signal from an EM sensor of the pacing device;
determining a time period between a non-ambulatory ventricular pace (VP) event and a mechanical response based on the non-ambulatory EM signal;
determining an optimal EM response time based the determined time period;
delivering an ambulatory pacing therapy from the pacing device;
sensing an ambulatory EM signal from the EM sensor of the pacing device;
determining a current EM response time in response to the sensed ambulatory EM signal;
comparing the current EM response time to the optimal EM response time; and
adjusting a pacing parameter setting of the ambulatory pacing therapy in response to the comparing.

* * * * *